(12) United States Patent
Zhu et al.

(10) Patent No.: US 12,161,646 B2
(45) Date of Patent: Dec. 10, 2024

(54) POLYCYCLIC CARBAMOYLPYRIDONE DERIVATIVES, PHARMACEUTICAL COMPOSITIONS AND USE THEREOF

(71) Applicant: JIAXING ANDICON BIOTECH CO., LTD., Jiaxing (CN)

(72) Inventors: Xiaoyun Zhu, Jiangsu (CN); Weiping Jiang, Jiangsu (CN)

(73) Assignee: JIAXING ANDICON BIOTECH CO., LTD., Jiaxing (CN)

( * ) Notice: Subject to any disclaimer, the term of this patent is extended or adjusted under 35 U.S.C. 154(b) by 1029 days.

(21) Appl. No.: 17/044,079

(22) PCT Filed: Apr. 11, 2019

(86) PCT No.: PCT/CN2019/082195
§ 371 (c)(1),
(2) Date: Sep. 30, 2020

(87) PCT Pub. No.: WO2019/196891
PCT Pub. Date: Oct. 17, 2019

(65) Prior Publication Data
US 2021/0093640 A1    Apr. 1, 2021

(30) Foreign Application Priority Data
Apr. 11, 2018  (CN) .......................... 201810323355.2

(51) Int. Cl.
| | | |
|---|---|---|
| *A61K 31/5383* | (2006.01) | |
| *A61K 31/13* | (2006.01) | |
| *A61K 31/196* | (2006.01) | |
| *A61K 31/351* | (2006.01) | |
| *A61K 31/426* | (2006.01) | |
| *A61K 31/4965* | (2006.01) | |
| *A61K 31/506* | (2006.01) | |
| *A61K 31/53* | (2006.01) | |
| *A61K 39/395* | (2006.01) | |
| *A61K 45/06* | (2006.01) | |
| *A61P 31/16* | (2006.01) | |
| *C07D 471/14* | (2006.01) | |
| *C07D 491/22* | (2006.01) | |
| *C07D 498/14* | (2006.01) | |

(52) U.S. Cl.
CPC .......... *A61K 31/5383* (2013.01); *A61K 31/13* (2013.01); *A61K 31/196* (2013.01); *A61K 31/351* (2013.01); *A61K 31/426* (2013.01); *A61K 31/4965* (2013.01); *A61K 31/506* (2013.01); *A61K 31/53* (2013.01); *A61K 39/39533* (2013.01); *A61K 45/06* (2013.01); *A61P 31/16* (2018.01); *C07D 471/14* (2013.01); *C07D 491/22* (2013.01); *C07D 498/14* (2013.01); *C07B 2200/05* (2013.01)

(58) Field of Classification Search
None
See application file for complete search history.

(56) References Cited

FOREIGN PATENT DOCUMENTS

| | | |
|---|---|---|
| CN | 107709321 A | 2/2018 |
| CN | 108440564 A | 8/2018 |
| CN | 109503625 A | 3/2019 |
| EP | 3290424 A1 | 3/2018 |
| RU | 2013114189 A | 10/2014 |
| WO | 2018030463 A1 | 2/2018 |

OTHER PUBLICATIONS

Knunyants, I. L., Chemical Encyclopedic Dictionary, Moscow Soviet Encyclopedia, 1983.
Tung, Robert D., "Deuterium medicinal chemistry comes of age", Future Medicinal Chemistry 2016, 8(5), 491-494.
May 14, 2021, First Office Action of Russian application 2020136675.
May 5, 2021 First Office Action of AU2019252208.
Oct. 15, 2021 Second Office Action issued in Russian application No. 2020136675.
Jul. 11, 2019 International Search Report issued in International Patent Application No. PCT/CN2019/082195.
Jul. 11, 2019 Written Opinion of the International Searching Authority issued in International Patent Application No. PCT/CN2019/082195.

(Continued)

*Primary Examiner* — Samantha L Shterengarts
(74) *Attorney, Agent, or Firm* — Verrill Dana, LLP

(57) ABSTRACT

The present invention discloses a group of polycyclic carbamoylpyridone derivatives, pharmaceutical compositions, and a use thereof. The structure of the polycyclic carbamoylpyridone derivatives of the present invention is represented by formula (VII). The polycyclic carbamoylpyridone derivative of the present invention functions as an inhibitor of influenza 5'cap-like structure (CAP)-dependent endonuclease activity and can be used to treat a cold caused by the influenza virus. The present invention also discloses a pharmaceutical composition to inhibit proliferation of the influenza virus.

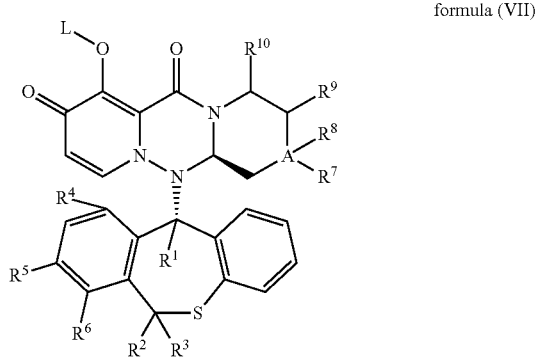

formula (VII)

19 Claims, No Drawings

(56) References Cited

OTHER PUBLICATIONS

Wang, Shizhen. "Non-official translation: Part VI search Research of Nuclear Medicine", Molecular Nuclear Medicine (2nd edition)), Apr. 30, 2004, pp. 417-418.
Rajsner et al. "Antidepressant fluorinated prothiadene derivatives: 9-Fluoro and 2,9-difluoro derivative of 11-(3-dimethylaminopropylidene)-6, 11-dihydrodibenzo[b,e]thiepin" Collection of Czechoslovak Chemical Communications, 1982, vol. 47,#1,p. 65-71.
Olga M.Rochovansky, "RNA Synthesis by Ribonucleoprotein-Polymerase Complexes Isolated from Influenza Virus" Virology. 1976, 73(2):327-38.
Shizhen Wang,—"Molecular Nuclear Medicine (The second version)"— pp. 417~418, 2004.
Mar. 18, 2019, First Office Action of Chinese Patent Application 2018103233552.
Jun. 5, 2019, Second Office Action of Chinese Patent Application 2018103233552.

POLYCYCLIC CARBAMOYLPYRIDONE DERIVATIVES, PHARMACEUTICAL COMPOSITIONS AND USE THEREOF

This application claims the benefit of Chinese patent application CN201810323355.2 filed on Apr. 11, 2018. The contents of the Chinese patent application are hereby incorporated by reference in their entireties.

TECHNICAL FIELD

The present disclosure relates to polycyclic carbamoylpyridone derivatives, pharmaceutical compositions, and their uses.

BACKGROUND ARTS

Influenza is an acute viral infection that can easily spread among people. The influenza infections especially reach peak during winter in temperate regions. Since the influenza virus is prevalent worldwide and can infect anyone of any age group, it often causes serious concurrent diseases and deaths in high-risk groups, which is currently a serious public health problem. According to statistics, the annual influenza pandemic causes about 3 to 5 million severe cases and about 250,000 to 500,000 deaths.

Because the influenza virus genome is very tiny, the influenza virus relies on the host cells' translation system to synthesize required proteins. Therefore, the messenger RNA (mRNA) of influenza virus needs to have both a 5'cap (CAP) structure and a 3'-poly(A) tail structure that can be recognized by the translation system of the host cell. Among them, the 5'cap structure is "snatched" from the 5'end of the host cell precursor mRNA by the endonuclease activity of the PA subunit in the influenza virus RNA polymerase complex. This method, called "CAP-snatching", captures the CAP cap structure of the host's mRNA for transcription of the virus's own mRNA, which is necessary for the initiation of influenza virus transcription.

Because "CAP-snatching" is a key part in the replication cycle of influenza virus, and there is no similar mechanism and corresponding protease in host cells, inhibitors of "CAP-snatching" endonuclease can selectively block the transcription process of influenza virus without affecting the host cell at the same time. As a result, this mechanism makes it become a potential anti-influenza drug target. The present disclosure satisfies these needs and provides other related advantages.

Content of the Present Disclosure

The present disclosure provides a polycyclic carbamoylpyridone derivative as shown in formula (VII), a stereoisomer thereof, a tautomer thereof, a hydrate thereof, a solvate thereof, an active metabolite thereof, a crystal form thereof, a pharmaceutically acceptable salt thereof, or a prodrug thereof, formula (VII)

wherein,
$R^1$ is hydrogen or deuterium;
$R^2$ is hydrogen or deuterium;
$R^3$ is hydrogen or deuterium;
L is hydrogen, alkyl, or (methoxycarbonyl)oxymethyl (i.e., —CH$_2$OC(=O)OCH$_3$);
and at least one of $R^1$, $R^2$ and $R^3$ is deuterium;
$R^4$ is hydrogen or halogen (preferably chlorine);
$R^5$ is hydrogen or halogen (preferably fluorine);
$R^6$ is hydrogen or halogen (preferably fluorine);
A is C or O, when A is C, then both $R^7$ and $R^8$ are hydrogen or both $R^7$ and $R^8$ are methyl; when A is O, then $R^7$ and $R^8$ do not exist;
$R^9$ is hydrogen or methyl; $R^{10}$ is hydrogen or methyl;
and $R^4$, $R^5$ and $R^6$ are not hydrogen simultaneously.

Preferably, the polycyclic carbamoylpyridone derivative as shown in formula (VII) satisfies any one of the following conditions:
condition 1: $R^4$ is hydrogen; R is fluorine; $R^6$ is fluorine; A is O; $R^9$ is hydrogen; $R^{10}$ is hydrogen;
condition 2: $R^4$ is hydrogen; $R^5$ is fluorine; $R^6$ is hydrogen; A is O; $R^9$ is hydrogen; $R^1$ is methyl and the configuration of the carbon atom directly connected with $R^{10}$ is (S);
condition 3: $R^4$ is chlorine; $R^5$ is hydrogen; $R^6$ is hydrogen; A is O; $R^9$ is hydrogen; $R^{10}$ is hydrogen;
condition 4: $R^4$ is hydrogen; $R^5$ is fluorine; $R^6$ is fluorine; A is C; both $R^7$ and $R^8$ are methyl; $R^9$ is hydrogen; $R^{10}$ is hydrogen;
condition 5: $R^4$ is hydrogen; $R^5$ is fluorine; $R^6$ is fluorine; A is C; both $R^7$ and $R^8$ are hydrogen; $R^9$ is hydrogen and the configuration of the carbon atom directly connected with $R^9$ is (R); $R^{10}$ is hydrogen;
condition 6: $R^4$ is hydrogen; $R^5$ is fluorine; $R^6$ is hydrogen; A is C; both $R^7$ and $R^8$ are hydrogen; $R^9$ is hydrogen; $R^{10}$ is hydrogen.

In the present disclosure, when L is alkyl, then the alkyl is preferably C1-4 alkyl, and further preferably methyl, ethyl, propyl, isopropyl, butyl, isobutyl or tert-butyl.

The present disclosure provides a polycyclic carbamoylpyridone derivative as shown in formula (I), a stereoisomer thereof, a tautomer thereof, a hydrate thereof, a solvate thereof, an active metabolite thereof, a crystal form thereof, a pharmaceutically acceptable salt thereof, or a prodrug thereof, Formula (I)

wherein:
$R^1$ is hydrogen or deuterium;
$R^2$ is hydrogen or deuterium;
$R^3$ is hydrogen or deuterium;

L is hydrogen, alkyl or (methoxycarbonyl)oxymethyl (i.e., —CH$_2$OC(=O)OCH$_3$);

and at least one of R$^1$, R$^2$ and R$^3$ is deuterium.

The polycyclic carbamoylpyridone derivative as shown in formula (I) is preferably selected from the following compounds:

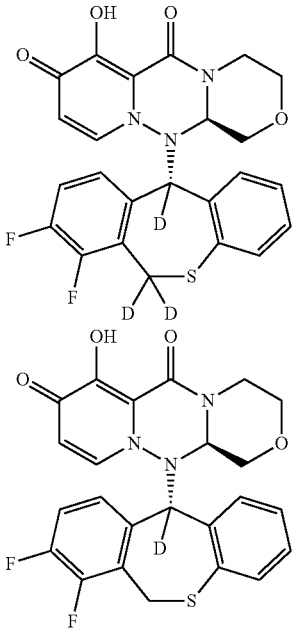

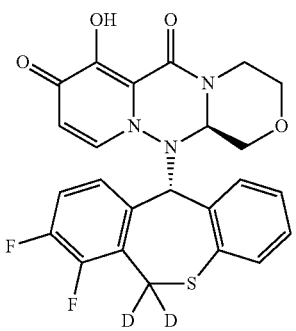

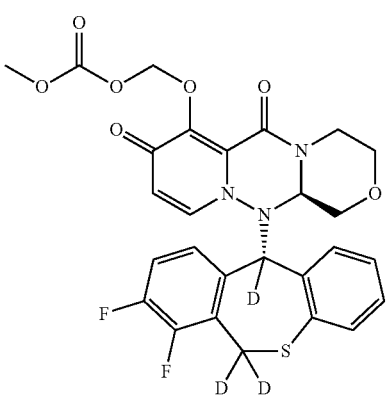

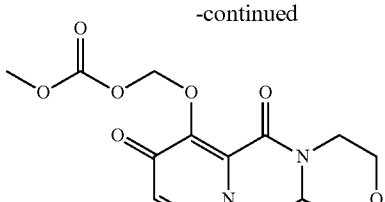

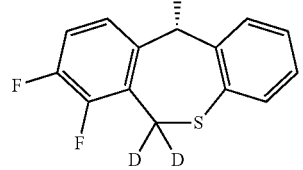

The present disclosure provides a polycyclic carbamoylpyridone derivative as shown in formula (II), a stereoisomer thereof, a tautomer thereof, a hydrate thereof, a solvate thereof, an active metabolite thereof, a crystal form thereof, a pharmaceutically acceptable salt thereof, or a prodrug thereof,

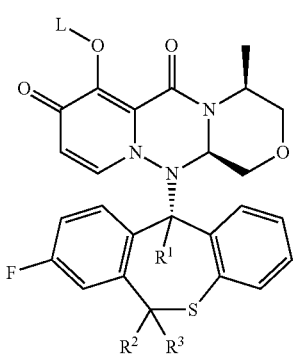

formula (II)

wherein:

R$^1$ is hydrogen or deuterium;

R$^2$ is hydrogen or deuterium;

R$^3$ is hydrogen or deuterium;

L is hydrogen, alkyl or (methoxycarbonyl)oxymethyl (i.e., —CH$_2$OC(=O)OCH$_3$);

and at least one of R$^1$, R$^2$ and R$^3$ is deuterium.

The polycyclic carbamoylpyridone derivative as shown in formula (II) is preferably selected from following compounds:

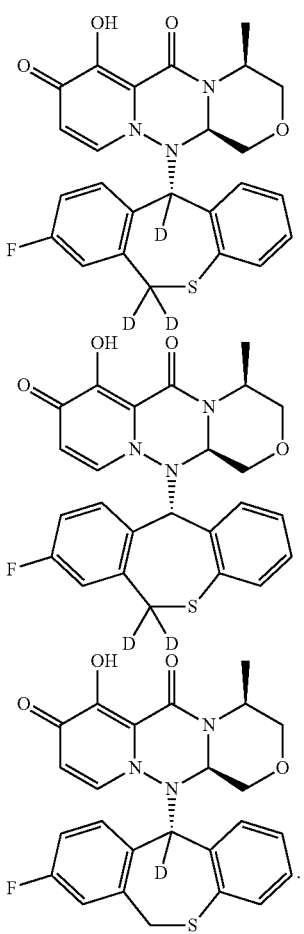

The present disclosure provides a polycyclic carbamoylpyridone derivative as shown in formula (III), a stereoisomer thereof, a tautomer thereof, a hydrate thereof, a solvate thereof, an active metabolite thereof, a crystal form thereof, a pharmaceutically acceptable salt thereof, or a prodrug thereof, formula (III)

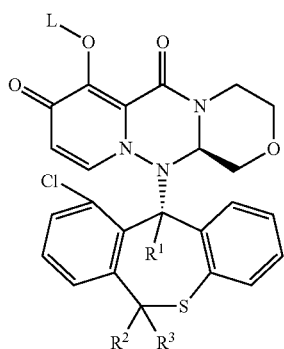

wherein:
R¹ is hydrogen or deuterium;
R² is hydrogen or deuterium;
R³ is hydrogen or deuterium;
L is hydrogen, alkyl or (methoxycarbonyl)oxymethyl (i.e., —CH₂OC(=O)OCH₃);
and at least one of R¹, R² and R³ is deuterium.

The polycyclic carbamoylpyridone derivative as shown in formula (III) is preferably selected from the following compounds:

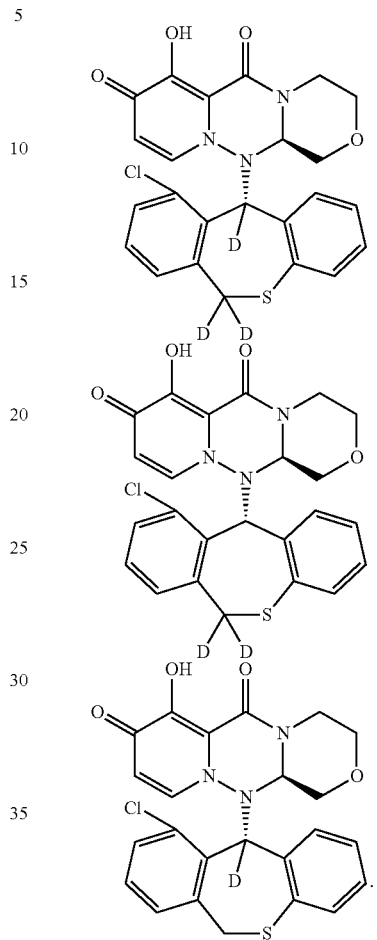

The present disclosure provides a polycyclic carbamoylpyridone derivative as shown in formula (IV), a stereoisomer thereof, a tautomer thereof, a hydrate thereof, a solvate thereof, an active metabolite thereof, a crystal form thereof, a pharmaceutically acceptable salt thereof, or a prodrug thereof, formula (IV)

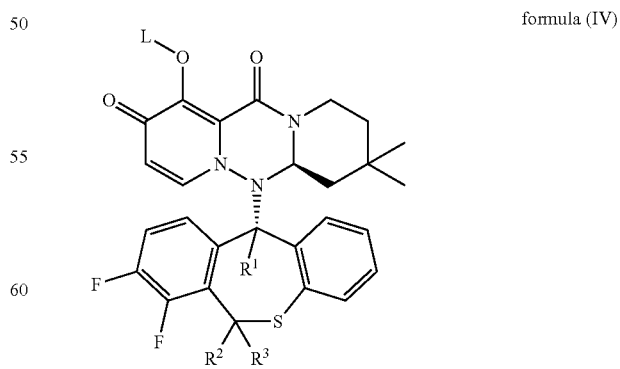

wherein:
R¹ is hydrogen or deuterium;
R² is hydrogen or deuterium;

R³ is hydrogen or deuterium;

L is hydrogen, alkyl or (methoxycarbonyl)oxymethyl (i.e., —CH₂OC(=O)OCH₃);

and at least one of R¹, R² and R³ is deuterium.

The polycyclic carbamoylpyridone derivative as shown in formula (IV) is preferably selected from the following compounds:

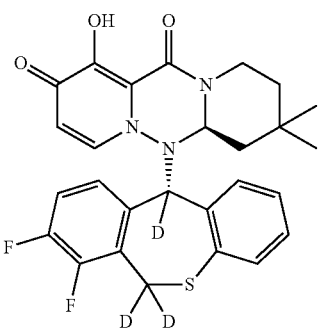

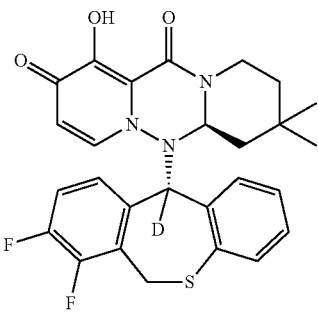

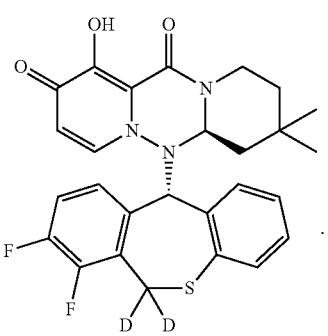

The present disclosure provides a polycyclic carbamoylpyridone derivative as shown in formula (V), a stereoisomer thereof, a tautomer thereof, a hydrate thereof, a solvate thereof, an active metabolite thereof, a crystal form thereof, a pharmaceutically acceptable salt thereof, or a prodrug thereof,

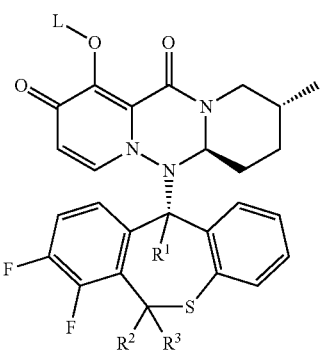

formula (V)

wherein:
R¹ is hydrogen or deuterium;
R² is hydrogen or deuterium;
R³ is hydrogen or deuterium;
L is hydrogen, alkyl or (methoxycarbonyl)oxymethyl (i.e., —CH₂OC(=O)OCH₃);
and at least one of R¹, R² and R³ is deuterium.

The polycyclic carbamoylpyridone derivative as shown in formula (V) is preferably selected from the following compounds:

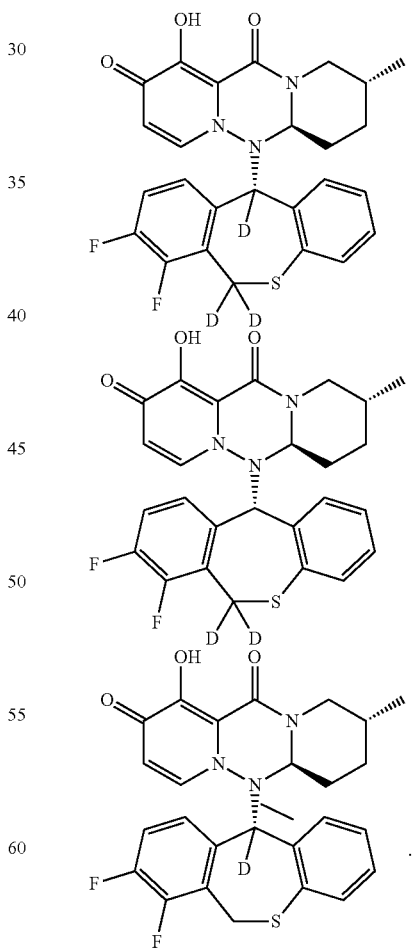

The present disclosure provides a polycyclic carbamoylpyridone derivative as shown in formula (VI), a stereoisomer thereof, a tautomer thereof, a hydrate thereof, a solvate thereof, an active metabolite thereof, a crystal form thereof, a pharmaceutically acceptable salt thereof, or a prodrug thereof, formula (VI)

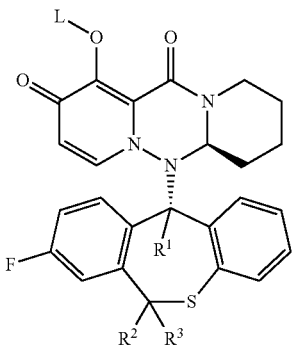

wherein:

$R^1$ is hydrogen or deuterium;

$R^2$ is hydrogen or deuterium;

$R^3$ is hydrogen or deuterium;

L is hydrogen or (methoxycarbonyl)oxymethyl (i.e., —CH$_2$OC(=O)OCH$_3$);

and at least one of $R^1$, $R^2$ and $R^3$ is deuterium.

The polycyclic carbamoylpyridone derivative as shown in formula (VI) is preferably selected from the following compounds:

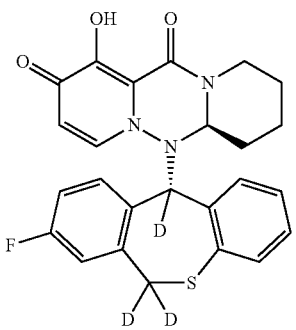

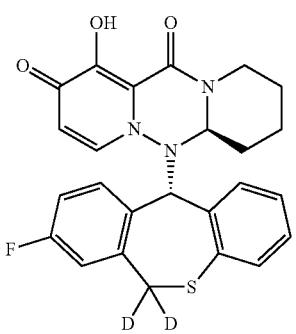

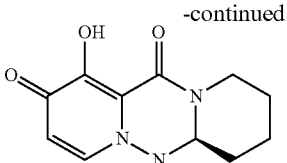

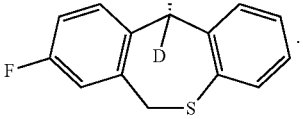

Unless otherwise specified, the term "alkyl" is used to indicate a linear or branched chain saturated hydrocarbon group, it can be monovalent (such as methyl), divalent (such as methylene) or multivalent (such as methine). Examples of alkyl include methyl (Me), ethyl (Et), propyl (such as n-propyl and isopropyl), butyl (such as n-butyl, isobutyl, s-butyl and t-butyl), pentyl (such as n-pentyl, isopentyl and neopentyl), and the like.

The compounds of the present disclosure are usually used in the form of free acid or free base. Alternatively, the compounds of the present disclosure can be used in the form of acid or base addition salts. The acid addition salt of the compounds of the present disclosure with free amino group (s) can be prepared by methods well known in the art, and can be prepared from organic and inorganic acids. Suitable organic acids include maleic acid, fumaric acid, benzoic acid, ascorbic acid, succinic acid, methanesulfonic acid, acetic acid, trifluoroacetic acid, oxalic acid, propionic acid, tartaric acid, salicylic acid, citric acid, gluconic acid, lactic acid, mandelic acid, phenylacetic acid, aspartic acid, stearic acid, palmitic acid, glycolic acid, glutamic acid and benzenesulfonic acid. Suitable inorganic acids include hydrochloric acid, hydrobromic acid, sulfuric acid, phosphoric acid, and nitric acid. Basic salts include salts formed with carboxylate anions, and include those formed with e.g., organic and inorganic cations selected from alkali metal ions, alkaline earth metal ions (for example, lithium, sodium, potassium, magnesium, barium, calcium) and ammonium ions, and substituted derivatives thereof (for example, dibenzylammonium, benzylammonium, 2-hydroxyethylammonium, etc.). Therefore, the term "pharmaceutically acceptable salt" of formula (I), formula (II), formula (III), formula (IV), formula (V), formula (VI) or formula (VII) shall include all acceptable salt forms.

In addition, prodrugs are also included within the scope of the present disclosure. A prodrug is any covalently linked carrier and releases the compound as shown in formula (I), formula (II), formula (III), formula (IV), formula (V), formula (VI) or formula (VII) in vivo when administered to a patient. Prodrugs are usually prepared by modifying functional groups in a way that allows the modification to be conventionally exchanged or decomposed in vivo to give the parent compound. Prodrugs include, for example, the compounds of the present disclosure in which a hydroxyl, amino, or sulfhydryl group is combined with any group, wherein the group is removed to give the hydroxyl, amino, or sulfhydryl group when the compound is administered to a patient.

Therefore, representative examples of prodrugs include, but are not limited to, acetate, formate and benzoate derivatives of alcohol and amine functional groups of the compounds as shown in formula (I), formula (II), formula (III), formula (IV), formula (V), formula (VI) or formula (VII). In addition, in the case of carboxylic acid (—COOH), esters such as methyl ester, ethyl ester, and the like may be included. In the case of hydroxyl, mixed anhydrides such as methoxy, ethoxy, propoxy, tert-butoxy and the like may be included.

For stereoisomers, the compounds as shown in formula (I), formula (II), formula (III), formula (IV), formula (V), formula (VI) or formula (VII) can have a chiral center, and can exist as racemates, racemic mixtures, and individual enantiomers or diastereomers. All isomeric forms are included in the present disclosure, including mixtures thereof. In addition, certain crystal forms of the compounds as shown in formula (I), formula (II), formula (III), formula (IV), formula (V), formula (VI) or formula (VII) can exist in the form of polymorphs, which are also included in the present disclosure. In addition, some of the compounds as shown in formula (I), formula (II), formula (III), formula (IV), formula (V), formula (VI) or formula (VII) can also be combined with water or other organic solvents to form a solvate. Such solvates are similarly included within the scope of the present disclosure.

Those skilled in the art should understand that any compound can contain unnatural proportions of atomic isotopes on one or more of the atoms constituting the compound. In the polycyclic carbamoylpyridone derivatives involved in the present disclosure, the deuteration means that the atoms at the relevant sites of the compound contain deuterium atoms in a proportion exceeding the natural ratio (that is, exceeding the natural abundance of deuterium). Therefore, any polycyclic carbamoylpyridone derivative that contains deuterium atoms at a ratio higher than the natural abundance of deuterium at the relevant site falls within the protection scope of the present disclosure. For example, it can be understood that the corresponding polycyclic carbamoylpyridone derivatives with certain deuteration rate or deuterium content, which are obtained by introducing deuterium atoms with commercially available deuterated reagents via the same or similar chemical synthesis methods shown in the embodiments of the present disclosure, are all within the protection scope of the present disclosure. The chemical synthesis methods and deuterated reagents herein are not limited to those exemplified in the examples, but should be understood as all synthetic methods or routes that can be used in the art to obtain the compounds of the present disclosure, and all deuterated reagent that can introduce deuterium atom(s) into the target molecules via the aforementioned synthetic methods or routes.

According to the specific embodiments of the present disclosure disclosed below, those skilled in the art can use the same or similar principles and methods to prepare the specific compounds of the polycyclic carbamoylpyridone derivatives as shown in formula (I), formula (II), formula (III), formula (IV), formula (V), formula (VI) or formula (VII).

The present disclosure further provides a use of the polycyclic carbamoylpyridone derivative as shown in formula (VII) (preferably formula (I), formula (II), formula (III), formula (IV), formula (V), or formula (VI)), the stereoisomer thereof, the tautomer thereof, the hydrate thereof, the solvate thereof, the active metabolite thereof, the crystal form thereof, the pharmaceutically acceptable salt thereof, or the prodrug thereof in the manufacture of a 5'cap-dependent endonuclease inhibitor.

The present disclosure further provides a use of the polycyclic carbamoylpyridone derivative as shown in formula (VII) (preferably formula (I), formula (II), formula (III), formula (IV), formula (V), or formula (VI)), the stereoisomer thereof, the tautomer thereof, the hydrate thereof, the solvate thereof, the active metabolite thereof, the crystal form thereof, the pharmaceutically acceptable salt thereof, or the prodrug thereof in the manufacture of a medicament for preventing, treating and/or alleviating a disease related to 5'cap-dependent endonuclease. Wherein the disease related to 5'cap-dependent endonuclease refers to symptoms and/or diseases that are prevented, treated and/or alleviated by inhibiting the level of 5'cap-dependent endonuclease in vivo, specifically refers to symptoms and/or diseases caused by influenza virus infection. More specifically, the influenza virus includes, but is not limited to, type A, B, and C. The symptoms include, but are not limited to, for example, cold-like symptoms such as fever, chill, headache, muscle pain, general fatigue, and the like, or respiratory tract inflammations such as sore throat, runny nose, nasal congestion, cough, sputum, and the like; gastrointestinal symptoms such as abdominal pain, vomiting, diarrhea, and the like; and further complications of secondary infection such as acute encephalopathy, pneumonia, and the like.

The present disclosure further provides a method for preventing, treating and/or alleviating a disease related to 5'cap-dependent endonuclease, the method comprises administering a therapeutically effective amount of the polycyclic carbamoylpyridone derivative as shown in formula (VII) (preferably formula (I), formula (II), formula (III), formula (IV), formula (V), or formula (VI)), the stereoisomer thereof, the tautomer thereof, the hydrate thereof, the solvate thereof, the active metabolite thereof, the crystal form thereof, the pharmaceutically acceptable salt thereof, or the prodrug thereof to an individual in need thereof to inhibit the in vivo level of 5'cap-dependent endonuclease of the individual. Wherein, the disease related to 5'cap-dependent endonuclease is specifically as described above.

The present disclosure further provides a pharmaceutical composition, which comprises a therapeutically effective amount of the polycyclic carbamoylpyridone derivative as shown in formula (VII) (preferably formula (I), formula (II), formula (III), formula (IV), formula (V), or formula (VI)), the stereoisomer thereof, the tautomer thereof, the hydrate thereof, the solvate thereof, the active metabolite thereof, the crystal form thereof, the pharmaceutically acceptable salt thereof, or the prodrug thereof, and a pharmaceutically acceptable carrier.

The present disclosure further provides a pharmaceutical composition, which not only comprises a therapeutically effective amount of the polycyclic carbamoylpyridone derivative as shown in formula (VII) (preferably formula (I), formula (II), formula (III), formula (IV), formula (V), or formula (VI)), the stereoisomer thereof, the tautomer thereof, the hydrate thereof, the solvate thereof, the active metabolite thereof, the crystal form thereof, the pharmaceutically acceptable salt thereof, or the prodrug thereof, and a pharmaceutically acceptable carrier, but also comprises other active pharmaceutical ingredient. The other active pharmaceutical ingredient is selected from neuraminidase inhibitors (such as oseltamivir, zanamivir, peramivir, Inavir and the like), RNA-dependent RNA polymerase inhibitors (such as favipiravir), M2 protein inhibitors (amantadine), PB2 Cap binding inhibitors (such as VX-787), anti-HA antibodies (MHAA4594A), or immune action drugs (nitazoxanide).

The compounds of the present disclosure can be used in combination with other pharmaceutical preparations in order to enhance the efficacy of the compounds or reduce the dosage of the compounds. For example, in the case of influenza, they can be used in combination with neuraminidase inhibitors (such as oseltamivir, zanamivir, peramivir, Inavir, and the like), RNA-dependent RNA polymerase inhibitors (such as favipiravir), M2 Protein inhibitors (amantadine), PB2 Cap binding inhibitors (VX-787), anti-HA antibodies (MHAA4594A), or immune action drugs (nitazoxanide), etc.

The pure forms or appropriate pharmaceutical compositions of the compounds of the present disclosure or pharmaceutically acceptable salts thereof can be administered by any acceptable administration mode of a drug with similar effects. The pharmaceutical composition of the present disclosure can be prepared by combining the compound of the present disclosure with a suitable pharmaceutically acceptable carrier, diluent or excipient, and can be formulated into a solid, semi-solid, liquid or gaseous preparation, such as tablet, capsule, powder, granule, ointmens, solution, suppository, injection, inhalant, gel, microsphere and aerosol. Typical administration routes of the pharmaceutical composition include, but are not limited to, oral, topical, transdermal, inhalation, parenteral, sublingual, buccal, rectal, vaginal and intranasal administration. As used herein, the term parenteral includes subcutaneous injection, intravenous, intramuscular, intrasternal injection or infusion techniques. The pharmaceutical composition of the present disclosure is formulated to allow the active ingredients contained therein to be bioavailable after the composition is administered to the patient. The composition to be administered to an individual or patient can have one or more dosage unit forms, wherein, for example, a tablet can have a single dosage unit, and a container containing the compound of the present disclosure in the form of an aerosol can contain multiple dosage units. The actual method for preparing the dosage form is known or will be known to those skilled in the art. The composition to be administered will in any case contain a therapeutically effective amount of the compound of the present disclosure or a pharmaceutically acceptable salt thereof, so as to treat the concerned disease or condition according to the teachings of the present disclosure.

The pharmaceutical composition of the present disclosure may be in solid or liquid form. In one aspect, the carrier is microparticles, so that the composition is, for example, in the form of a tablet or powder. The carrier can be a liquid, and the composition is, for example, an oral syrup, an injectable liquid, or an aerosol suitable for, such as inhalation administration. When intended to be taken orally, the pharmaceutical composition is preferably in a solid or liquid form, wherein semi-solid, semi-liquid, suspension and gel forms are considered to be included in the solid or liquid form herein. For oral solid compositions, the pharmaceutical composition can be formulated into powder, granule, compressed tablet, pill, capsule, chewable tablet, powder tablet and the like. Such solid compositions usually contain one or more inert diluents or edible carriers. In addition, one or more of the following substances may also be present: binders, such as carboxymethyl cellulose, ethyl cellulose, microcrystalline cellulose, xanthan gum or gelatin; excipients, such as starch, lactose or dextrin; disintegrants, such as alginic acid, sodium alginate, Primogel, corn starch, etc.; lubricants, such as magnesium stearate or hydrogenated vegetable oil (Sterotex); glidants, such as colloidal silicon dioxide; sweeteners, for example, sucrose or saccharin; flavoring agents such as peppermint, methyl salicylate or orange flavoring agents; and coloring agents.

When the pharmaceutical composition is in the form of a capsule, such as a gelatin capsule, it may contain a liquid carrier such as polyethylene glycol or oil in addition to the above-mentioned types of substances. The pharmaceutical composition may be in liquid form, such as tincture, syrup, solution, emulsion or suspension. This liquid can betaken orally, or delivered by injection, as two examples. When it is intended to be taken orally, the composition preferably contains one or more of sweeteners, preservatives, dyes/colorants and flavor enhancers in addition to the compound of the present disclosure. In the composition intended to be administered by injection, one or more of surfactants, preservatives, wetting agents, dispersants, suspending agents, buffers, stabilizers and isotonic agents may be contained.

Whether the liquid pharmaceutical composition of the present disclosure is in a solution, suspension or other similar form, it can contain one or more of the following adjuvants: sterile diluent, such as water for injection, normal saline solution, preferably normal saline, Ringer's solution, isotonic sodium chloride, non-volatile oil (e.g., synthetic monoglycerides or diglycerides, which can be used as solvents or suspension media), solvents such as polyethylene glycol, glycerol, propylene glycol; antibacterial agents, such as benzyl alcohol or methyl p-hydroxybenzoate; antioxidants, such as ascorbic acid or sodium bisulfite; chelating agents, such as ethylenediaminetetraacetic acid; buffers, such as acetate salts, citrate salts, or phosphate salts, and regents for adjusting tonicity, such as sodium oxide or dextrose. The parenteral preparation can be packaged in an ampoule, disposable syringe or multi-dose vial made of glass or plastic. Normal saline is the best adjuvant. The injectable pharmaceutical composition is preferably sterile.

The liquid pharmaceutical composition of the present disclosure to be administered parenterally or orally should contain a certain amount of the compound of the present disclosure so that a suitable dosage can be obtained. The pharmaceutical composition of the present disclosure may be intended for topical administration, in which case the carrier preferably comprises a solution, an emulsion, an ointment or a gel base. For example, this base may contain one or more of the following: paraffin oil, lanolin, polyethylene glycol, beeswax, mineral oil, diluent (such as water and alcohol), and emulsifier and stabilizer. Thickener may be present in pharmaceutical composition for topical administration. If transdermal administration is intended, the composition may include a transdermal patch or iontophoresis device.

The pharmaceutical composition of the present disclosure may be intended for rectal administration, taking the form of a suppository as an example, a suppository will melt in the rectum and release the drug. The composition for rectal administration may contain an oily base as a suitable non-irritating excipient. The base includes, but is not limited to, lanolin, cocoa butter, and polyethylene glycol.

The pharmaceutical composition of the present disclosure may contain various substances that modify the physical form of a solid or liquid dosage unit. For example, the composition may contain a substance that forms a coating shell around the active ingredient. The substance that forms a coating shell is generally inert and may be selected from, for example, sugar, shellac and other enteric coating agents. Alternatively, the active ingredient can be enclosed in gelatin capsules.

The pharmaceutical composition of the present disclosure in solid or liquid form may contain an agent that binds the compound of the present disclosure and thereby aids delivery of the compound. Suitable reagents with this ability include monoclonal or polyclonal antibodies, proteins or liposomes.

The pharmaceutical composition of the present disclosure may consist of a dosage unit that can be administered in the form of an aerosol. The term aerosol is used to denote a variety of systems from colloidal types to systems consisting of pressurized packaging. Delivery can be by liquefied or compressed gas, or by a suitable pump system that dispenses the active ingredient. Aerosols of the compounds of the present disclosure can be delivered in a single-phase, two-phase or three-phase system to deliver the active ingredient. The side delivery of the aerosol includes necessary containers, starters, valves, sub-containers, etc., which together can form a kit. Those skilled in the art can determine the preferred aerosol without undue experiments.

The pharmaceutical composition of the present disclosure can be prepared by methods well known in the pharmaceutical field. For example, a pharmaceutical composition to be administered by injection can be prepared by combining the compound of the present disclosure with sterile distilled water to form a solution. Surfactants can be added to facilitate the formation of a uniform solution or suspension. Surfactants are compounds that non-covalently interact with the compounds of the present disclosure, thereby promoting the dissolution or uniform suspension of the compounds in an aqueous delivery system.

The compounds of the present disclosure or pharmaceutically acceptable salts thereof are administered in a therapeutically effective amount, and the therapeutically effective amount will vary depending on various factors, including the activity of the specific compounds used, the metabolic stability of the compounds and the length of action time, and the age, weight, general health status, gender and diet of the patient, administration mode and time, excretion rate, drug combination, severity of a specific disease or condition, and individuals subjected to therapy.

The compounds of the present disclosure or pharmaceutically acceptable derivatives thereof may also be administered simultaneously, before or after the administration of one or more other therapeutic agents. This combination therapy includes administration of a single pharmaceutical formulation containing the compound of the present disclosure and one or more other active agents, and administration of separate pharmaceutical formulations of the compound of the present disclosure and each active agent. For example, the compound of the present disclosure and another active agent may be administered to a patient together in a single oral administration composition (for example, a tablet or capsule), or each agent may be administered in a separate oral administration formulation. In the case of using separate administration formulations, the compound of the present disclosure and one or more additional active agents can be administered substantially at the same time (i.e., simultaneously) or at separate staggered times (i.e., successively). Combination therapy should be understood as including all these schemes.

The dosage of the pharmaceutical combination of the present disclosure can be adjusted according to the disease state, route of administration, age or weight of the patient. For oral administration to adults, it is usually 0.1 to 100 mg/kg/day, preferably 1 to 20 mg/kg/day. The appropriate dosage of the present disclosure needs to be determined in consideration of the patient's age, weight, condition, route of administration, etc., oral administration is usually in the range of 0.05 to 100 mg/kg/day, preferably 0.1 to 10 mg/kg/day. In the case of non-oral administration, the dosage of the pharmaceutical composition of the present disclosure varies greatly according to different administration routes, but is usually 0.005 to 10 mg/kg/day, preferably 0.01 to 1 mg/kg/day.

The dosage of the compound of the present disclosure varies according to the method of administration, the patient's age, weight, state, and the type of disease, but generally for oral administration, the dosage per day for adults is about 0.05 mg to 3000 mg, preferably about 0.1 mg to 1000 mg, and can be administered separately as needed.

In addition, in the case of non-oral administration, the dosage per day for adults is about 0.01 mg to 1000 mg, preferably about 0.05 mg to 500 mg. It should be understood that, in the present disclosure, the combination of substituents and/or variables of the chemical formula is allowed only if it produces a stable compound.

The present disclosure relates to substituted polycyclic carbamoylpyridone derivatives with 5'cap structure (CAP) dependent endonuclease inhibitory activity, prodrugs thereof, deuterated compounds thereof, and pharmaceutical compositions containing the same, and the method of using the composition to inhibit the proliferation of influenza virus.

The compounds of the present disclosure are prodrug, and therefore have the following advantages: high oral absorption, good bioavailability, good clearance rate, and high lung metastasis, and the like. Therefore, they can form an excellent drug.

The parent compounds of the compounds of present disclosure have high inhibitory activity against 5'cap structure-dependent endonuclease, and since the endonuclease is a virus-specific enzyme, the compounds will have high selectivity and can be a drug with reduced side effects. Further, the compounds of the present disclosure and/or the parent compounds of the compounds of the present disclosure have the following advantages, i.e., high metabolic stability, high solubility, high oral absorbability, good bioavailability, good clearance rate, high lung metastasis, long half-life, high non-protein binding rate, low inhibition against hERG channel, low inhibition against drug metabolizing enzymes of liver, confirmed cytopathic effect (CPE) inhibitory effect, and/or being negative in phototoxicity test, Ames test and in the genotoxicity test, or no liver toxicity, etc., so the compounds of the present disclosure have better pharmacological properties.

The compounds of the present disclosure and/or the compounds of the present disclosure can be used for symptoms and/or diseases caused by influenza viruses, and are effective to treat and/or prevent, e.g., cold-like symptoms such as fever, chills, headache, muscle pain, general fatigue, and the like, or respiratory tract inflammations such as sore throat, runny nose, nasal congestion, cough, phlegm, and the like, gastrointestinal symptoms such as abdominal pain, vomiting, diarrhea, and the like, further complications of secondary infections such as acute encephalopathy, pneumonia and the like, and improve symptoms thereof.

Unless otherwise specified, the reagents and raw materials used in the present disclosure are commercially available.

Unless otherwise specified, the compounds of the present disclosure are named manually or by ChemDraw® software, and the commercially available compounds use their vendor directory names.

In conformity with common knowledge in the art, the above-mentioned preferred conditions can be combined arbitrarily to obtain preferred embodiments of the present disclosure.

DETAILED DESCRIPTION OF THE EMBODIMENT

The following preferred examples further illustrate the present disclosure, but the present disclosure is not limited thereto. In the following examples, the experimental methods without indicating specific conditions are conducted according to conventional methods and conditions, or according to the product specification.

The raw materials are commercially available, or prepared by methods known in the art, or prepared according to the methods described herein.

Example 1
The synthetic route is as follows:
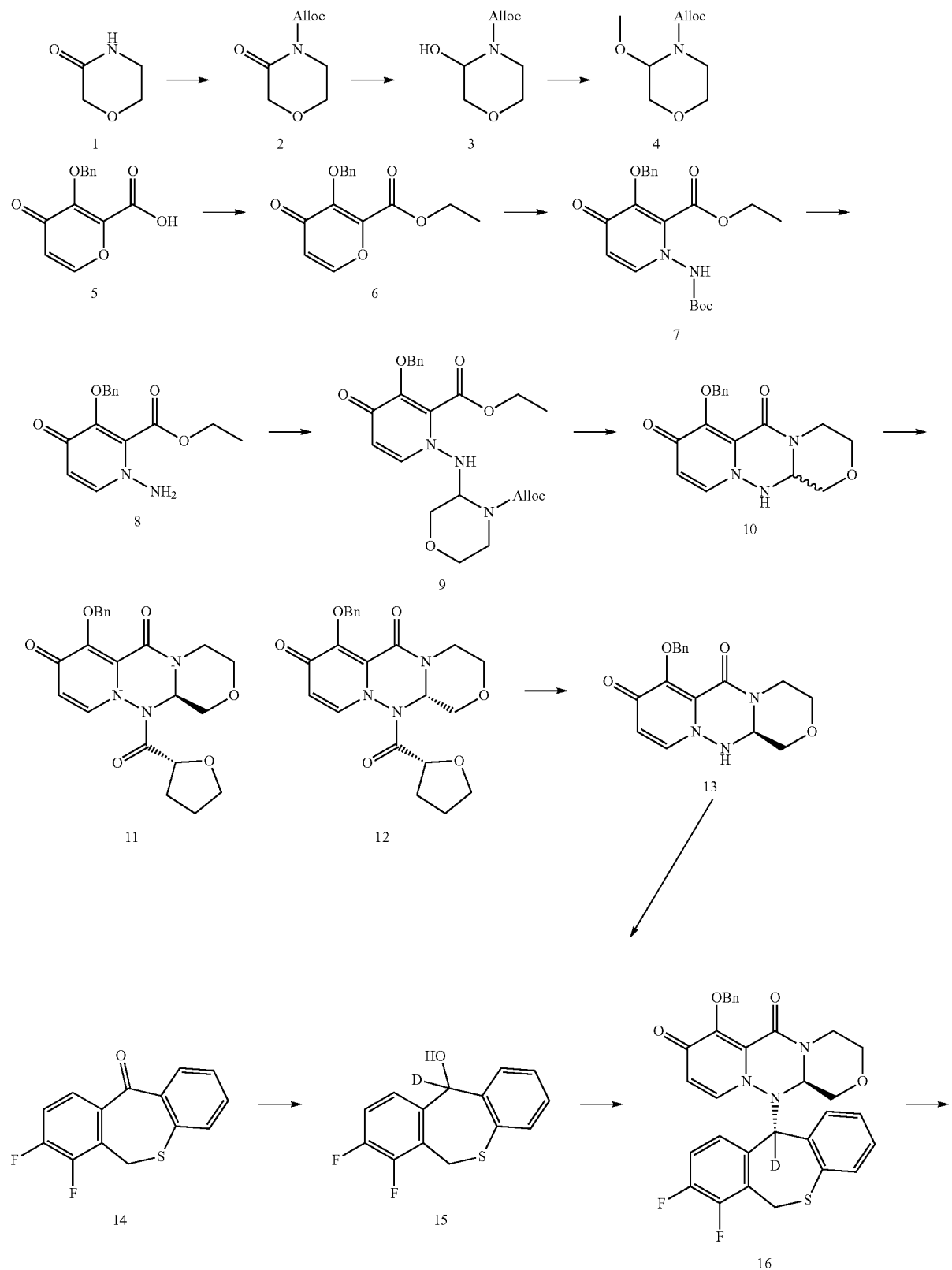

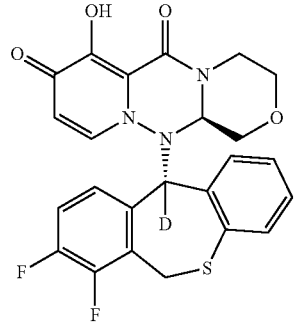

Example 1A

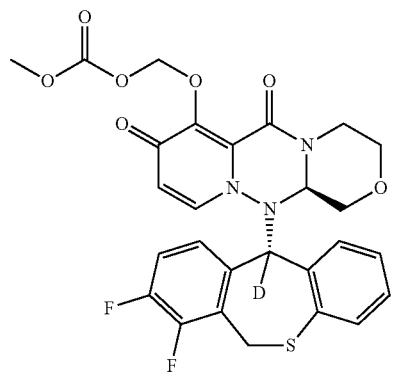

Example 1B

Preparation of Intermediate 15

156 g of intermediate 14 (purchased from Nanjing Leizheng Pharmaceutical Technology Co., Ltd., also can be prepared by referring to Rajsner et al., *Collection of Czechoslovak Chemical Communications*, 1987, vol. 47, #1, p. 65-71) was dissolved in 2.5 L of THF, and 14 g of lithium tetrahydroaluminate-D4 was added slowly at 0° C. The resulting mixture was warmed to room temperature, and stirred for 3 hours. After the completion of the reaction monitored by TLC, 2N hydrochloric acid was added to the reaction mixture. The mixture was extracted with ethyl acetate, and concentrated under reduced pressure. The residue was slurried with cyclohexane/dichloromethane to obtain intermediate 15 as a white solid. MS: ESI 266.1[M+1]$^+$.

Preparation of Intermediate 16

257 g of intermediate 13 and 244.3 g of intermediate 15 were suspended in a solution (803 g) of 50 wt % propyl phosphoric anhydride in ethyl acetate, and 280 mL of ethyl acetate was added. Methanesulfonic acid (109 g) was added to the reaction mixture at room temperature, and the resulting mixture was stirred under reflux for 6 hours. Water was added to the reaction mixture under cooling of an ice bath. After stirring at room temperature for 1 hour, THF was added, and the obtained mixture was extracted with ethyl acetate. The organic layer was washed with water and then 8% sodium bicarbonate aqueous solution, and concentrated under reduced pressure. The obtained solid was dissolved in 1.4 L of THF, added with 198 g of potassium carbonate. After the temperature was raised to 50° C., 60 mL of benzyl bromide was added dropwise, and the mixture was stirred at 60° C. for 9 hours. 2 N aqueous solution of hydrochloric acid was added dropwise to the reaction mixture under cooling of an ice bath, and the mixture was stirred at room temperature, extracted with ethyl acetate. The organic layer was washed with water and then 8% sodium bicarbonate aqueous solution, and dried over anhydrous magnesium sulfate, added with activated carbon for adsorption for 1 hour, filtered with diatomaceous earth, and the filtrate was concentrated under reduced pressure. The concentrated solution was slurried with ethyl acetate/hexane, during which a solid precipitated. The mixture was filtered and the obtained solid was dried to obtain intermediate 16 with a yield of 45%. MS: ESI 575.2[M+H]$^+$.

Example Compound 1A

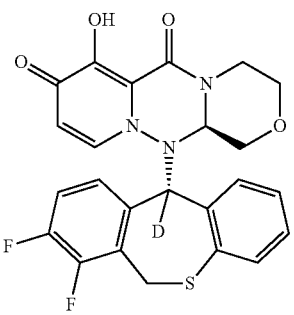

15 g of lithium chloride was added to 120 mL of a solution of intermediate 16 (40 g) in DMA at 25° C., and the mixture was stirred at 80° C. for 3 hours. Acetone, 0.5 N dilute hydrochloric acid solution and water were added to the reaction mixture at 0 to 5° C., and stirred for 1.5 hours, during which a solid precipitated. The mixture was filtered, and the obtained solid was recrystallized with chloroform/isopropyl ether, filtered and dried to obtain example compound 1 A with a yield of 79%. MS: ESI 485.1[M+H]$^+$. $^1$H-NMR (CDCl$_3$) δ: 3.00-3.51 (2H, m), 3.62 (1H, t), 3.83 (2H, m), 4.60 (2H, m), 5.28-5.33 (2H, m), 5.78-6.72 (2H, m), 6.86-6.90 (1H, m), 6.70-7.18 (5H, m). Deuteration rate: 99.6%.

Example Compound 1B

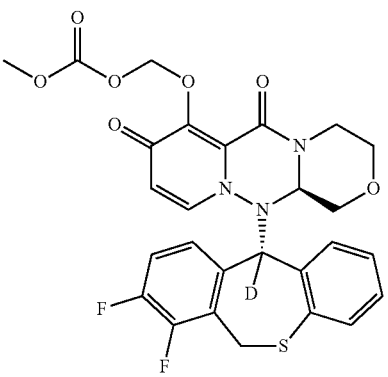

To example compound 1 A (5.0 g) was added DMA (25 mL) and stirred, then methyl chloromethyl carbonate (2.4 g), potassium carbonate (2.9 g), and potassium iodide (1.7 g) were added. The resulting mixture was heated to 50° C. and stirred for 6 hours. DMA (5 mL) was added and the stirring was continued for 6 hours. The reaction mixture was cooled to room temperature, added with DMA (25 mL), stirred at 50° C. for 5 minutes, and filtered. 1 mol/L hydrochloric acid aqueous solution (50 mL) and water (15 mL) were added dropwise to the filtrate at 0 to 5° C. and stirred for 1 hour. The mixture was filtered and the obtained solid was dried under reduced pressure at 60° C. to obtain example compound 1B with a yield of 88%. MS: ESI 573.1 [M+H]⁺.
¹H-NMR (DMSO-D₆) δ: 2.89-3.28 (2H, m), 3.41 (1H, t), 3.68 (1H, m), 3.70 (3H, s), 3.97-4.39 (2H, m), 4.42 (1H, m), 5.39-5.68 (2H, m), 5.71-5.74 (3H, m), 6.81-7.00 (2H, J=6.9 Hz), 7.08-7.45 (5H, m). Deuteration rate: 99.6%.

Example Compound 1C

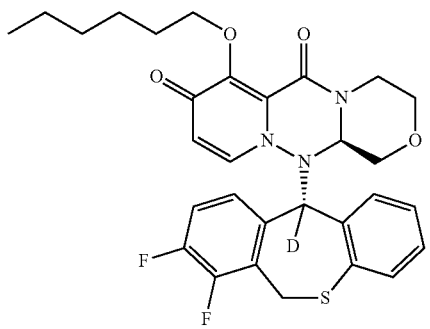

To example compound A (4.8 g) was added DMA (30 mL) and stirred, and then bromohexane (1.7 g), potassium carbonate (2.9 g), and potassium iodide (1.7 g) were added. The mixture was heated to 50° C. and stirred for 6 hours. DMA (5 mL) was added and the stirring was continued for 6 hours. The reaction mixture was cooled to room temperature, DMA (30 mL) was added, and the mixture was stirred at 50° C. for 5 minutes, and filtered. 1 mol/L hydrochloric acid aqueous solution (50 mL) and water (25 mL) were added dropwise to the filtrate at 0 to 5° C. and stirred for 1 hour. The mixture was filtered to obtain a solid, and the solid was dried under reduced pressure at 60° C. to obtain example compound 1C with a yield of 79%. MS: ESI 569.2[M+H]⁺.

Example 2

The synthetic route is as follows:

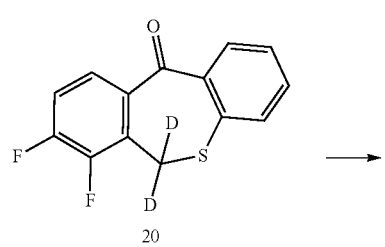

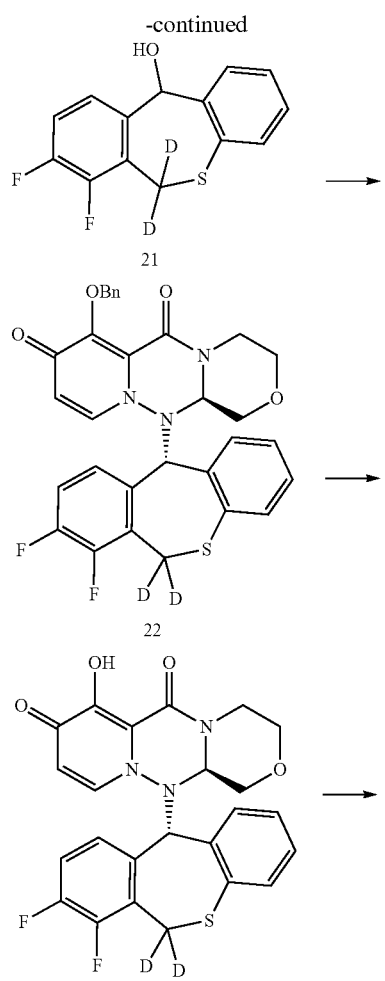

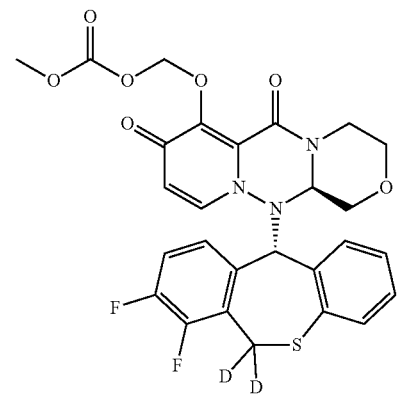

Example 2B

Intermediate 20 was purchased from Nanjing Leizheng Pharmaceutical Technology Co., Ltd., and can also be prepared by referring to Rajsner et al., *Collection of Czechoslovak Chemical Communications*, 1987, vol. 47, #1, p. 65-71. MS: ESI 265.5[M+H]⁺.

The intermediate 21 was prepared by referring to the preparation process of intermediate 15 except that lithium tetrahydroaluminate-D4 was replaced with lithium tetrahydroaluminate, and intermediate 14 was replaced with intermediate 20.

The intermediate 22 was prepared by referring to the preparation process of intermediate 16 except that intermediate 15 was replaced with intermediate 21.

Preparation of Example 2A

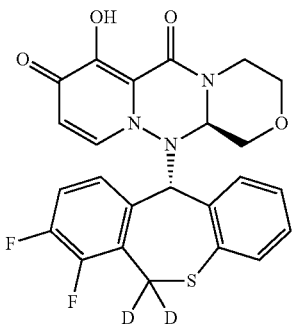 [SMILES: [2H]C1([2H])Sc2ccccc2[C@@H](N2[C@@H]3COCCN3C(=O)c3c(O)c(=O)ccn32)c2ccc(F)c(F)c21]

To 120 mL of a solution of intermediate 22 (40 g) was added 15 g of lithium chloride at 25° C., and the mixture was stirred at 80° C. for 3 hours. Acetone, 0.5 N dilute hydrochloric acid solution and water were added to the reaction mixture at 0 to 5° C. and stirred for 1.5 hours, during which a solid precipitated. The mixture was filtered, and the obtained solid was recrystallized with chloroform/isopropyl ether, filtered and dried to obtain example compound 2 A with a yield of 65%. MS: ESI 486.1[M+H]$^+$. H-NMR (CDCl$_3$) δ: 3.01-3.50 (2H, m), 3.61 (1H, t), 3.80 (2H, m), 4.02 (1H, m), 4.58 (2H, m), 5.76-6.70 (2H, m), 6.85-6.8/8 (1H, m), 6.70-7.20 (5H, m). Deuteration rate: 98.6%.

Example Compound 2B

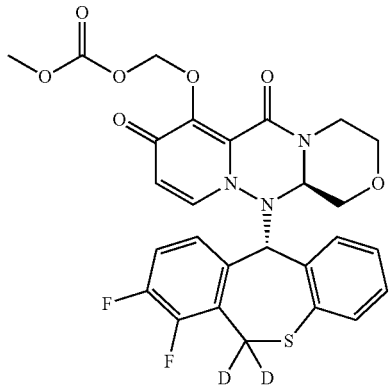 [SMILES: [2H]C1([2H])Sc2ccccc2[C@@H](N2[C@@H]3COCCN3C(=O)c3c(OCOC(=O)OC)c(=O)ccn32)c2ccc(F)c(F)c21]

DMA (50 mL) was added to example compound 2 A (10.0 g) and stirred, and then methyl chloromethyl carbonate (4.8 g), potassium carbonate (6.0 g), potassium iodide (3.4 g) were added. The mixture was heated to 50° C. and stirred for 6 hours. DMA (10 mL) was added and the stirring was continued for 6 hours. The reaction mixture was cooled to room temperature, DMA (50 mL) was added, and the mixture was stirred at 50° C. for 5 minutes, and filtered. 1 mol/L hydrochloric acid aqueous solution (100 mL) and water (30 mL) were added dropwise to the filtrate at 0 to 5° C. and stirred for 1 hour. The mixture was filtered to obtain a solid and the solid was dried under reduced pressure at 60° C. to obtain example compound 2B with a yield of 90%. MS: ESI 574.2[M+H]$^+$. $^1$H-NMR (DMSO-D$_6$) δ: 2.91-3.30 (2H, m), 3.44 (1H, t), 3.71 (1H, m), 3.73 (3H, s), 4.02-4.41 (3H, m), 4.43 (1H, m), 5.43-5.76 (2H, m), 5.79 (1H, m), 6.84-7.05 (2H, J=6.9 Hz), 7.10-7.49 (5H, m). Deuteration rate: 99.6%.

Example 3

The synthetic route is as follows:

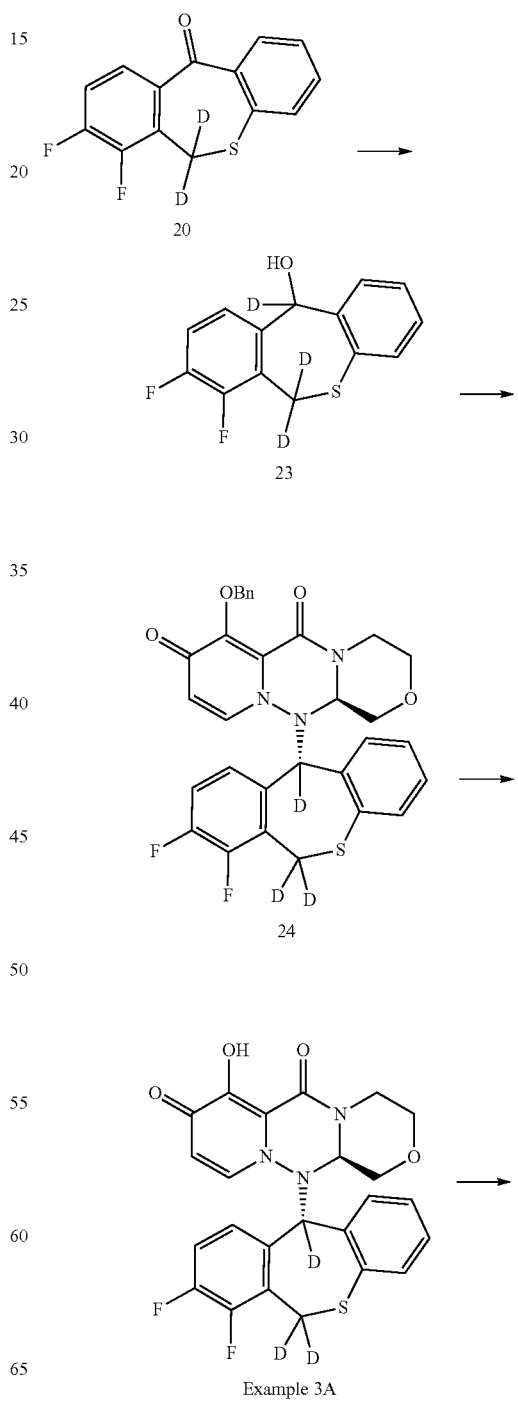

Example 3A

-continued

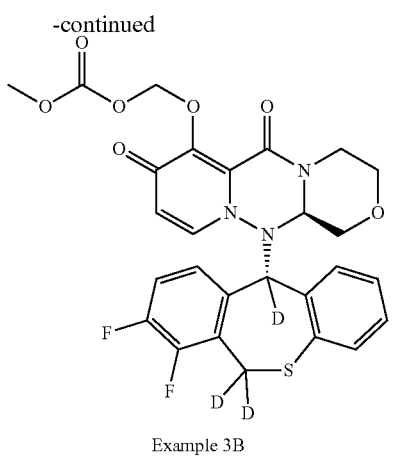

Example 3B

The intermediate 23 was prepared by referring to the preparation process of intermediate 15, the difference was that intermediate 14 was replaced with intermediate 20.

The intermediate 24 was prepared by referring to the preparation process of intermediate 16, the difference was that intermediate 15 was replaced with intermediate 23.

Preparation of Example 3A

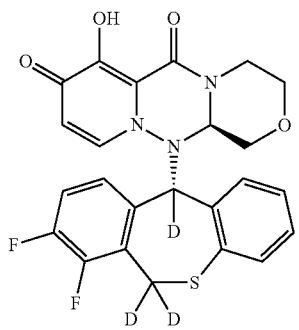

The example compound 3 A was prepared by referring to the preparation process of compound 1A, the difference was that intermediate 16 was replaced with intermediate 24. MS: ESI 487.1[M+H]$^+$. Deuteration rate: 99.5%.

Preparation of Example 3B

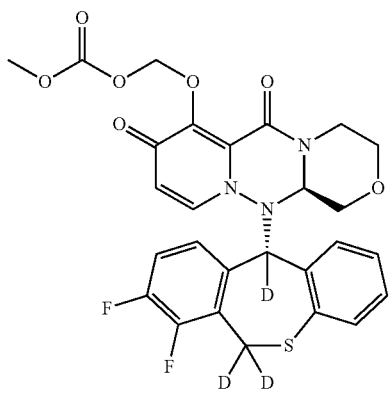

The example compound 3B was prepared by referring to the preparation process of compound 1B, the difference was that compound 1 A was replaced with compound 3A. MS: ESI 575.2[M+H]$^+$. Deuteration rate: 99.6%.

Preparation of Intermediate 2

50 g of intermediate 1 was dissolved in 1 L of THF, 305 mL of a solution of n-butyllithium in hexane was added under N$_2$ atmosphere at −78° C., and the mixture was stirred at −78° C. for 2 hours. A solution of 59.6 g of allyl chloroformate in THF (200 mL) was added dropwise to the reaction solution, and the mixture was stirred at −78° C. for 2 hours. The reaction solution was quenched in a saturated aqueous solution of ammonium chloride, and warmed to room temperature, followed by extraction with ethyl acetate. The organic layer was washed with saturated brine, dried, and concentrated under reduced pressure to remove solvent to obtain intermediate 2, with a yield of 76%.

Preparation of Intermediate 3

20 g of intermediate 2 was dissolved in 200 mL of THF, and 138 mL of a solution of DIBAL-H in hexane was added dropwise under N$_2$ atmosphere at −78° C., and the mixture was stirred at −78° C. for 1 hour. The reaction was quenched by adding an aqueous solution of sodium potassium tartrate and the mixture was extracted with ethyl acetate. The organic layer was washed with saturated brine, dried, and concentrated under reduced pressure to remove solvent to obtain intermediate 3.

Preparation of Intermediate 4

To a solution of intermediate 3 (12.4 g) in methanol (130 mL) was added p-toluenesulfonic acid monohydrate (1.3 g), and the mixture was stirred at room temperature for 8 hours. The reaction was quenched with aqueous sodium bicarbonate solution, concentrated, and extracted with ethyl acetate. The organic layer was washed with saturated brine and dried, followed by concentration under reduced pressure to remove solvent to obtain intermediate 4 with a yield of 88%. MS: ESI 202.2[M+H]$^+$.

Preparation of Intermediate 6

30 g of intermediate 5 was dissolved in 150 mL of DMF, and 15.2 g of iodoethane and 27.6 mL of diazabicycloundecene were added dropwise to the solution, and stirred at room temperature overnight. The reaction was quenched with 10% ammonium chloride aqueous solution and extracted with ethyl acetate. The organic layer was washed with saturated brine, dried, and concentrated under reduced pressure to obtain intermediate 6.

Preparation of Intermediate 7

2.5 g of the intermediate was dissolved in 25 mL of DMA solution, 6.9 g of pyridinium tosylate and 1.8 g of boc-hydrazine were added, and the mixture was stirred at 60° C. for 15 hours. Water was added, and the mixture was extracted with ethyl acetate. The organic layer was washed with saturated aqueous solution of ammonium chloride, and saturated aqueous solution of sodium chloride, dried, concentrated under reduced pressure, and subjected to flash silica gel column chromatography to obtain intermediate 7.

Preparation of Intermediate 8

2.5 g of compound 8 was dissolved in 4 N hydrogen chloride in ethyl acetate (25 mL). The mixture was stirred at room temperature for 1 hour, concentrated under reduced pressure, washed with saturated sodium bicarbonate aqueous solution, and extracted with dichloromethane. The organic layer was washed with saturated brine, dried, and concentrated under reduced pressure to obtain intermediate 8.

Preparation of Intermediate 10

Compound 4 (31 g) was dissolved in 820 mL of acetonitrile at −25° C. under nitrogen atmosphere, 40 g of intermediate 8 was added, tin tetrachloride (230 mL) was added dropwise, and the mixture was stirred at −25° C. for 45 minutes. After the reaction solution was quenched in aqueous sodium bicarbonate solution, dichloromethane was added. The mixture was stirred at room temperature, filtered through diatomaceous earth, and extracted with dichloromethane. The organic layer was washed with saturated brine, dried, and concentrated under reduced pressure to obtain crude intermediate 9. The crude intermediate 9 was dissolved in 800 mL of THF, morpholine (115 mL), and tetrakis(triphenylphosphine)palladium (150 g) were added, and the mixture was stirred at room temperature for 2.5 hours. Methyl tert-butyl ether was added to the reaction mixture, the mixture was filtered to obtain a solid, and the obtained solid was dried to obtain intermediate 10.

Preparation of Intermediate 11

(R)-tetrahydrofuran-2-carboxylic acid (855 mg, 7.36 mmol) and 40 g of intermediate 10 were sequentially dissolved in 180 mL of ethyl acetate at room temperature, 80 mL of pyridine and 50% propylphosphoric anhydride in ethyl acetate were added. The mixture was stirred for 8 hours, and filtered to obtain a solid. The solid was washed with ethyl acetate and ethanol, and slurried in 120 mL of ethanol at room temperature for 7 hours. The suspension was filtered and the filter cake was washed twice with ethanol to obtain crude intermediate 11.

Preparation of Intermediate 13

15 g of the crude intermediate 11 was suspended in ethanol (700 mL), DBU (10.5 mL) was added and the mixture was stirred for 30 minutes. 1.3 L of diisopropyl ether was added and stirred at room temperature for 30 minutes. The mixture was filtered and washed with ethyl acetate twice to obtain intermediate 13, with a yield of 91%. MS: ESI 328.1[M+H]$^+$.

Preparation of S-033188A

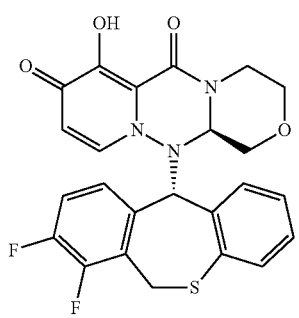 [SMILES: O=C1c2c(O)c(=O)ccn2N([C@@H]2c3ccccc3SCc3c2ccc(F)c3F)[C@@H]2COCCN12]

S-033188 A was prepared by referring to the preparation method of example compound 1A.

Ms: ESI 485.1[M+H]$^+$.

Preparation of S-033188B

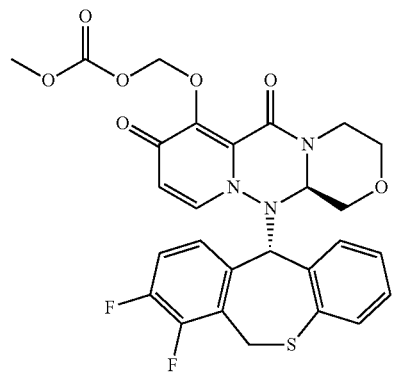 [SMILES: COC(=O)OCOc1c2n(ccc1=O)N([C@@H]1c3ccccc3SCc3c1ccc(F)c3F)[C@@H]1COCCN1C2=O]

S-033188B was prepared by referring to the preparation method of example compound 1B.

Ms: ESI 572.1[M+H]$^+$.

Compound in the Table:

The compounds in the following table and their single enantiomers, and prodrugs of the corresponding ester of the compounds in the following table were prepared by the processes similar as the above. Such esters can convert into active metabolites with hydroxyl group(s) in vivo through e.g., oral administration under the action of drug metabolizing enzymes, hydrolytic enzymes, digestive juice, or bacteria in the digestive tract, and the like. The corresponding esters of the compounds in the table are preferably but not limited to methyl methyl carbonate.

TABLE 1

| structure of the compounds in the table | |
|---|---|
| Structure of the compounds | Mass spectrometry |
| (structure shown) | 483.2 ESI [M + H]$^+$ |

TABLE 1-continued structure of the compounds in the table

| Structure of the compounds | Mass spectrometry |
|---|---|
| (structure) | 482.2 ESI [M + H]⁺ |
| (structure) | 481.2 ESI [M + H]⁺ |
| (structure) | 485.1 ESI [M + H]⁺ |
| (structure) | 484.1 ESI [M + H]⁺ |
| (structure) | 483.1 ESI [M + H]⁺ |
| (structure) | 513.2 ESI [M + H]⁺ |
| (structure) | 511.2 ESI [M + H]⁺ |
| (structure) | 512.2 ESI [M + H]⁺ |
| (structure) | 499.2 ESI [M + H]⁺ |

TABLE 1-continued structure of the compounds in the table

| Structure of the compounds | Mass spectrometry |
|---|---|
| | 498.2 ESI [M + H]+ |
| | 497.2 ESI [M + H]+ |
| | 467.5 ESI [M + H]+ |
| | 466.5 ESI [M + H]+ |

TABLE 1-continued structure of the compounds in the table

| Structure of the compounds | Mass spectrometry |
|---|---|
| | 465.5 ESI [M + H]+ |
| | |
| | |
| | |

TABLE 1-continued structure of the compounds in the table

| Structure of the compounds | Mass spectrometry |
|---|---|
| (structure shown) | |

Example 4: Determination of Cap-Dependent Endonuclease (CEN) Inhibitory Activity 1) Preparation of Substrate 30merRNA (5'-pp-[m2'-0]GAA UAU(-Cy3)GCA UCA CUA GUA AGCUUU GCU CUA-BHQ2-3', given by China Pharmaceutical University) in which the G at the 5'end was diphosphorylated, the hydroxyl at the 2'position was methoxylated, the U at the 6th position from the 5'end was labeled with Cy3, and the 3'end was labeled with BHQ2 was purchased. ScriptCap system was used to add cap structure to obtain a product of m7G[5']-ppp-[5'] [m2'-]GAA UAU(-Cy3)GCA UCA CUA GUA AGC UUU GCU CUA(-BHQ2)-3'. It was separated and purified by modified polyacrylamide gel electrophoresis and used as substrate.

2) Preparation of Enzyme

RNP was prepared from virus particles according to a prescribed method (Reference: VIROLOGY (1976) 73, pages 327-338. LGA M.ROCHOVANSKY). Specifically, 200 μL of 1×10³ PFU/mL A/WSN/33 virus was inoculated into 10-day-old developing chicken eggs, cultured at 37° C. for 2 days, and then the allantoic fluid of the chicken eggs was recovered. The virus particles were purified by ultracentrifugation with 20% sucrose, TritonX-100 and lysolecithin were used to dissolve the virus particles, and then separated by ultracentrifugation with 30% to 70% glycerol density gradients, the RNP fraction was collected (50% to 70% glycerol fraction), used as enzyme solution (containing about 1 nM of PB1 •PB2 •PA complex).

3) Enzymatic Reaction 2.5 μL of enzymatic reaction mixture (composition: 53 mM Tris hydrochloride (pH 7.8), 1 mM $MgCl_2$, 1.25 mM dithiothreitol, 80 mM NaCl, 12.5% glycerol, 0.15 μL enzyme solution) was dispensed in a 384-well plate made of polypropylene. Then, 0.5 μL of DMSO was added to 0.5 μL of the test compound solution serially diluted with DMSO, the positive control (PC) and the negative control (NC), and mixed thoroughly. Then 2 μL of substrate solution (1.4 nM substrate RNA, 0.05% Tween20) was added, and the reaction was initiated. The reaction mixture was incubated at room temperature for 60 minutes, and then 1 μL of the reaction mixture was added to 10 μL of high-purity formamide solution (containing GeneScan120LizSize Standard as sizing marker, manufactured by Applied Biosystem(ABI)) to terminate the reaction. The reaction of NC was stopped in advance by adding EDTA (4.5 mM) before the start of the reaction (all labeled concentrations were the final concentrations).

4) Determination of Inhibitory Rate ($IC_{50}$ Value)

After the reaction was terminated, the solution was heated at 85° C. for 5 minutes, quenched on ice for 2 minutes, and then analyzed with ABIPRIZM3730Genetic Analyzer (Genetic Analyzer). The peak of the cap-dependent endonuclease product was quantified by the analysis software ABI Genemapper, and the fluorescence intensity of PC and NC was used as 0% inhibition and 100% inhibition, respectively, the CEN reaction inhibitory rate (%) of the test compounds was calculated, and curve fitting software was used to calculate the $IC_{50}$ value.

Example 5: CPE Suppression Effect Confirmation Test

<Material>
1) 2% FCS E-MEM (prepared by adding kanamycin and FCS to MEM (minimum essential medium))
2) 0.5% BSA E-MEM (prepared by adding kanamycin and BSA to MEM (minimum essential medium))
3) HBSS (Hanks balanced salt solution)
4) MDBK cells: the cell density was adjusted to an appropriate value ($3\times10^5$/mL) with 2% FCS E-MEM
5) MDCK cells: the cells was washed twice with HBSS, and then the cell density was adjusted to an appropriate value ($5\times10^5$/mL) with 0.5% BSA E-MEM.
6) Trypsin solution
The trypsin (SIGMA) from porcine pancreas was dissolved with PBS(−), and filtered with a 0.45 μm filter.
7) Microplate reader
8) WST-8 kit
9) 10% SDS solution <Operation Process>

1) Dilution and Dispensing of Test Samples

2% FCS E-MEM was used as the culture medium for MDBK cells, and 0.5% BSA E-MEM was used as the culture medium for MDCK cells. In the following, the same culture medium was used for the dilution of viruses, cells, and test samples.

The test samples were diluted to an appropriate concentration with the culture solution in advance, and 2-5 times serial dilutions (50 μL/well) were prepared on a 96-well plate. Two plates were made for anti-influenza activity measurement and cytotoxicity measurement. The determination was performed in triplicate for each drug.

When MDCK cells were used, trypsin with a final concentration of 3 μg/mL was added to the cells only for the determination of the anti-influenza activity.

2) Dilution and Dispensing of Influenza Virus

The influenza virus was diluted with culture medium to an appropriate concentration in advance, and each was aliquoted at 50 μL/well into the 96-well plate containing the test sample. The culture solution was aliquoted to the plate for cytotoxicity measurement at 50 μL/well.

3) Dilution and Dispensing of Cells

The cells with the cell density adjusted to an appropriate value were aliquoted in an amount of 100 μL/well into the 96-well plate containing the test sample.

The mixture was mixed with a plate mixer. The cells were cultured in a $CO_2$ incubator for 3 days in both the anti-influenza activity test and the cytotoxicity test.

4) Dispensing of WST-8

The 96-well plate cultured for 3 days was observed with naked eyes and under a microscope, and the supernatant was removed from the plate in a manner that the cells were not suck away.

The WST-8 kit was 10-fold diluted with the culture medium, and 100 μL of each WST-8 solution was aliquoted into each well. The mixture was mixed with a plate mixer. The cells were then incubated in a $CO_2$ incubator for 1 to 3 hours.

For the plate for measuring anti-influenza activity, after incubation, 10 μL of 10% SDS solution was aliquoted into each well to inactivate the virus.

5) Determination of Absorbance

For the mixed 96-well plate, the absorbance was measured with EnVision at 450 nm/620 nm dual wavelength.

<Calculation of the Value of Each Measurement Item>

Based on the following calculation formula, the Microsoft Excel program was used for calculation.

Calculation of 50% cell death inhibitory concentration ($EC_{50}$) for influenza infection $$EC_{50}=10z$$

$$Z=(50\%\text{-High }\%)/(\text{High }\%\text{-Low }\%)\times\{\log(\text{High conc.})-\log(\text{Low conc.})\}+\log(\text{High conc.})$$

For the test substance (compounds of the examples) as the parent compound, the measurement results of Example 4 and Example 5 are shown in Table 2.

TABLE 2

| CEN inhibitory activity test and CPE inhibitory effect test results | | |
|---|---|---|
| Code of the compounds of the examples # | $CEN\_IC_{50}$ nM | $CPE\_EC_{50}$ nM |
| 1A | 1.14 | 0.68 |
| 2A | 1.89 | 1.24 |
| 3A | 1.65 | 0.60 |
| S-033188A | 2.01 | 1.22 |

From the above results, it can be seen that compounds 1A, 2A, and 3A show high cap-dependent endonuclease inhibitory activity and high CPE inhibitory effect, especially the CPE inhibitory effect of compound 1 A and compound 3 A are twice that of S-033188A. Therefore, the compounds of the examples can be prepared as drugs for preventing/treating symptoms/disease induced by influenza virus infection.

Example 6: Bioavailability Test

<Experimental Materials and Methods for Oral Absorption Research>

(1) Animals used: SD rats are used.
(2) Feeding conditions: SD rats were allowed to take in solid feed and purified water freely.
(3) Dosing amount and grouping setting: Oral or intravenous administration were performed at prescribed dosage. The groups were set as follows. (the dosage of each compound varied)
Oral administration 1 to 30 mg/kg (n=5 to 6)
Intravenous administration 0.5 to 10 mg/kg (n=5 to 6)
(4) Preparation of dosing solution: suspension was used for oral administration through intragastric administration. Solution was used for intravenous administration through tail vein.
(5) Evaluation items: Blood was collected overtime, and the concentrations of the drugs in plasma were determined by LC/MS/MS.
(6) Statistical analysis: For concentration changes in plasma, the area under the concentration-time curve (AUC) in plasma was calculated using the nonlinear least squares method, and the bioavailability (BA) was calculated from the AUC in the oral administration group and the intravenous administration group, and the elimination half-life of drug concentration in plasma through intravenous administration was counted.

The test results are shown in Table 3.

TABLE 3

| Bioavailability measurement results of the compounds of the examples | | |
|---|---|---|
| Code of the compounds of the examples # | The compounds of the examples BA% | Half-life through intravenous administration $T_{1/2}$ hour |
| 1A | 7.1 | 4.0 |
| 2A | 5.0 | 5.0 |
| 3A | 7.8 | 5.2 |
| S-033188A | 4.7 | 3.8 |
| 1B | 18.4 | — |
| 2B | 15.9 | — |
| 3B | 19.8 | — |
| S-033188B | 15.3 | — |

From the results in Table 3, it can be seen that the prodrugs (1B, 2B, 3B) have improved bioavailability compared with the parent compounds (1A, 2A, 3A). The compounds 1A, 2A, and 3 A of the examples have significantly improved bioavailability than S-033188A; and the bioavailability of the compounds 1B, 2B, and 3B of the examples have improved significantly than that of S-033188B. The elimination half-life of the example compounds through intravenous administration have prolonged at different degrees.

Therefore, the compounds of the present disclosure have better oral absorption than S-033188A/S-033188B, and can be used as a medicament for the treatment and/or prevention of symptoms and/or diseases caused by influenza virus infection, and are expected to have smaller dosage and lower side effects.

Example 7: hERG Test

In order to evaluate the risk of prolonged QT interval in electrocardiogram, HEK293 cells expressing human ether-a-go-go related gene (hERG) channel were used to study delayed rectifier K⁺ current ($I_{Kr}$) which plays an important role in the process of ventricular repolarization.

Fully automatic patch clamp system was used to record the $I_{Kr}$ caused by giving +50 mV depolarization stimulation for 2 seconds and further −50 mV repolarization stimulation for 2 seconds after keeping the cells at a membrane potential of −80 mV by the whole-cell patch clamp method. After the generated current is stabilized, the cells were treated with an extracellular fluid dissolved with the test substances at target concentrations (NaCl: 137 mmol/L, KCl: 4 mmol/L, $CaCl_2$: 1.8 mmol/L, $MgCl_2\text{-}6H_2O$: 1 mmol/L, glucose: 10 mmol/L, HEPES: 10 mmol/L, pH 7.4) at room temperature for 10 minutes. The absolute value of the maximum tail current was measured based on the current value of the resting membrane potential by using analysis software from the obtained $I_{Kr}$. Furthermore, the inhibitory rate with respect to the maximum tail current before the treatment of test substances was calculated, and compared with the medium application group (0.1% DMSO solution), and the influences of the test substances on IKr were evaluated.

TABLE 4

Inhibitory rates of the compounds of the examples under the condition of 0.3-10 μmol/L

| Code of the compounds of the examples # | Inhibitory rate % |
|---|---|
| 1A | 3.1 |
| 2A | 7.8 |
| 3A | 3.5 |
| S-033188A | 8.2 |

It can be seen from the results of inhibitory rate in Table 4 that the inhibitory rates of the compounds 1A, 2A, and 3 A of the examples are significantly lower than that of S-033188A, especially the inhibitory rates of 1 A and 3 A are less than half of S-033188A. The test results show that 1 A and 3 A have lower cardiotoxicity than compound S-033188A.

Example 8: Influenza Virus Infection Mice Lethal Inhibition Test

<Mouse>

BALB/cAnNCrlCrlj 6 to 7 week old mice were used in the experiment.

<Preparation of Virus Solution>

A/WS/33, A/Victoria/3/75 or B/Maryland/1/59 (ATCC) were passaged in the lungs of the mice to make mouse domesticated viruses. The cryopreserved mouse domesticated virus solutions were quickly thawed and diluted with DPBS to form the infectivity titer (A/WS/33: 800-4000TC ID501 mice, A/Victoria/3/75:750 $TCID_{50}$/mouse, B/Maryland/1/59: 100 $TCID_{50}$/mouse).

<Infection>

Under the anesthesia of the ketamine-xylazine mixture, 100 μL of the prepared virus solution was inoculated through the nose to directly infect the lungs of the mice.

<Preparation of Test Sample>

The test sample was suspended in 0.5% methylcellulose solution at an appropriate concentration.

<Administration to Infected Mice>

For mice just after infection with the virus or after a certain period of time, 200 μL of the diluted test sample was orally administered.

<Efficacy Evaluation>

After virus infection, the mice were raised for 14 days, and the daily administration amount $ED_{50}$ (mg/kg/day) required for 50% lethal suppression was calculated and compared with the control group to evaluate the virus suppression effect.

<Result>

Table 5 shows the $ED_{50}$ value in the case of single administration.

TABLE 5

$ED_{50}$ value in the case of single administration of the compounds of the examples

| Code of the compounds of the examples # | $ED_{50}$ mg/kg/day |
|---|---|
| 1B | 0.41 |
| 2B | 0.71 |
| 3B | 0.33 |
| S-033188B | 0.78 |

From the above results, it can be seen that all the tested compounds show various degrees of virus-inhibiting effects in vivo, especially the half effective doses of compound 1B and compound 3B are significantly less than S-033188B. It shows that the dosage of the compounds of the examples in clinical application will be less, or the medication interval will be longer, and the corresponding side effects will be also smaller, than that of S-033188B.

Example 9: Detection of Toxicity of Samples to MDCK Cells

The experiment uses alamarBlue® (Invitrogen) kit to detect the toxic effects of drugs on cells.

Experimental principle: The experiment uses alamarBlue® (Invitrogen) kit to detect the toxic effects of drugs on cells. AlamarBlue® is a redox indicator that produces changes in absorbance and fluorescent signals based on cellular metabolic activity. AlamarBlue® is freely soluble in water. After its oxidized form enters cells, it will be reduced by mitochondrial enzymes to produce measurable fluorescence and color changes. It is used for quantitative analysis of cell viability and cell proliferation, and for in vitro cytotoxicity studies. Normal cells with metabolic activity can convert the reagents to produce strong fluorescence and color changes. Damaged and inactive cells have lower natural metabolic activity and lower corresponding signals, so the strength of fluorescence signal can reflect the level of cell activity.

Experimental procedure: MDCK cells were seeded in a 96-well cell culture plate, and cultured till cell attachment for later use. The drug was serially 3 times diluted from 2 times the highest test concentration to 8 gradients. The drug was added to the cells and cultured in a $CO_2$ incubator at 37° C. After 48 hours of dosing and incubation, the cytopathic effect (CPE) caused by the drug was observed under a microscope. Then alamarBlue® medium was added to detect the survival rate of the cells. The toxicity of the drug to cells is inversely proportional to the activity of the cells and is expressed as the activity of the cells.

Calculation formula: cell activity (%)=(drug group-blank control)/(cell control-blank control)*100

The drug has a toxic effect on MDCK cells at very high concentrations. The concentration that causes 50% of the toxic effect is shown by $CC_{50}$. See the table below for details.

TABLE 6

Toxicity of the compounds of the examples on cells

| Code of the compounds of the examples # | $CC_{50}$ nM |
|---|---|
| 1A | 48285 |
| S-033188A | 29882 |

The toxicity of compound 1 A is significantly lower than that of S-033188A. It shows that compound 1 A has higher safety than S-033188A.

For those skilled in the art, the present disclosure is not limited to the foregoing illustrative examples, and can be embodied in other specific forms without departing from its essential attributes. Therefore, it is expected that all aspects should be regarded as illustrative examples referring to the appended claims rather than being limited to the foregoing examples, and the cited documents are only for the appended claims rather than the foregoing examples. All changes fallen into the equivalent meaning and scope of the claims are therefore expected to be included herein.

All patents, patent applications and literature references listed in this specification are hereby incorporated by reference in their entireties. In case of inconsistency, the present disclosure including definitions will be persuasive.

What is claimed is:

1. A polycyclic carbamoylpyridone derivative as shown in formula (VII), a stereoisomer thereof, a tautomer thereof, a hydrate thereof, a solvate thereof, a crystal form thereof, a pharmaceutically acceptable salt thereof, or a prodrug thereof,

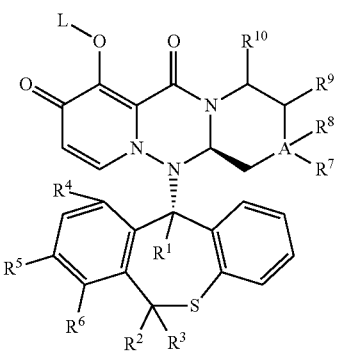

formula (VII)

wherein,
$R^1$ is hydrogen or deuterium;
$R^2$ is hydrogen or deuterium;
$R^3$ is hydrogen or deuterium;
L is hydrogen, alkyl, or (methoxycarbonyl) oxymethyl; and at least one of $R^1$, $R^2$ and $R^3$ is deuterium;
$R^4$ is hydrogen or halogen;
$R^5$ is hydrogen or halogen;
$R^6$ is hydrogen or halogen;
A is C or O, when A is C, then both $R^7$ and $R^8$ are hydrogen or both $R^7$ and $R^8$ are methyl;
when A is O, then $R^7$ and $R^8$ do not exist;
$R^9$ is hydrogen or methyl; $R^{10}$ is hydrogen or methyl;
and $R^4$, $R^5$ and $R^6$ are not hydrogen simultaneously.

2. The polycyclic carbamoylpyridone derivative as shown in formula (VII), the stereoisomer thereof, the tautomer thereof, the hydrate thereof, the solvate thereof, the crystal form thereof, the pharmaceutically acceptable salt thereof, or the prodrug thereof as defined in claim 1,
wherein the polycyclic carbamoylpyridone derivative as shown in formula (VII) satisfies any one of the following conditions:
condition 1: $R^4$ is hydrogen; $R^5$ is fluorine; $R^6$ is fluorine; A is O; $R^9$ is hydrogen; $R^{10}$ is hydrogen;
condition 2: $R^4$ is hydrogen; $R^5$ is fluorine; $R^6$ is hydrogen; A is O; $R^9$ is hydrogen; $R^{10}$ is methyl and the configuration of carbon atom directly connected with $R^{10}$ is(S);
condition 3: $R^4$ is chlorine; $R^5$ is hydrogen; $R^6$ is hydrogen; A is O; $R^9$ is hydrogen; $R^{10}$ is hydrogen;
condition 4: $R^4$ is hydrogen; $R^5$ is fluorine; $R^6$ is fluorine; A is C; both $R^7$ and $R^8$ are methyl; $R^9$ is hydrogen; $R^{10}$ is hydrogen;
condition 5: $R^4$ is hydrogen; $R^5$ is fluorine; $R^6$ is fluorine; A is C; both $R^7$ and $R^8$ are hydrogen; $R^9$ is hydrogen and the configuration of carbon atom directly connected with $R^9$ is (R); $R^{10}$ is hydrogen;
condition 6: $R^4$ is hydrogen; $R^5$ is fluorine; $R^6$ is hydrogen; A is C; both $R^7$ and $R^8$ are hydrogen; $R^9$ is hydrogen; $R^{10}$ is hydrogen.

3. A polycyclic carbamoylpyridone derivative as shown in formula (I), formula (II), formula (III), formula (IV), formula (V), or formula (VI), a stereoisomer thereof, a tautomer thereof, a hydrate thereof, a solvate thereof, a crystal form thereof, a pharmaceutically acceptable salt thereof, or a prodrug thereof,

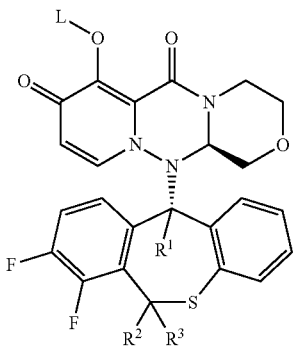

formula (I)

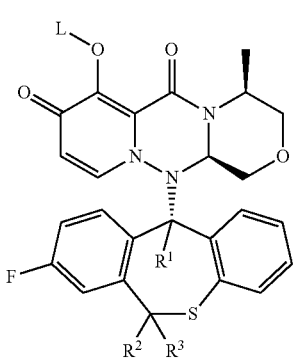

formula (II)

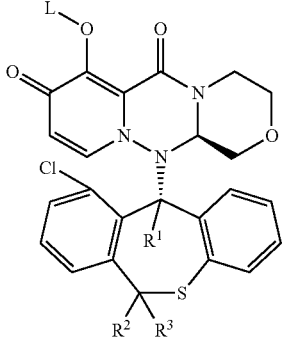

formula (III)

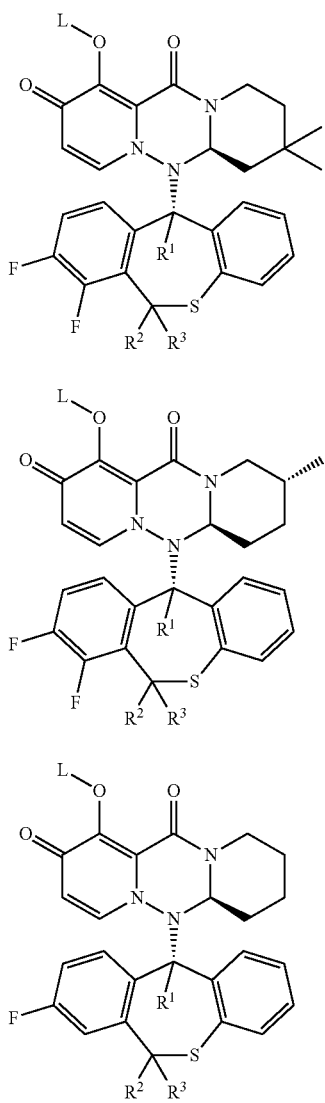

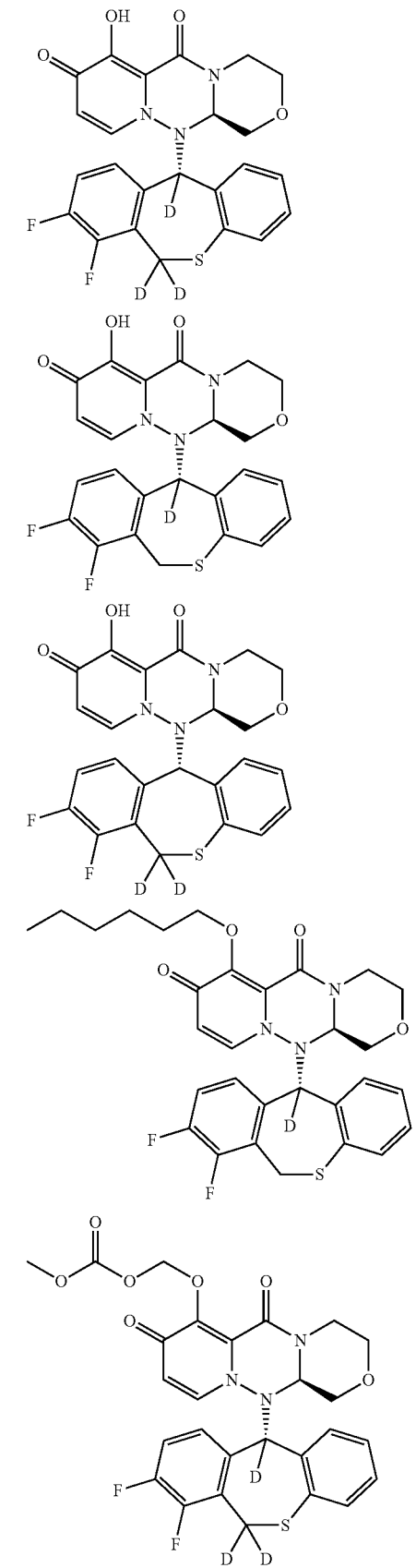

in the formula (I), formula (II), formula (III), formula (IV), formula (V), or formula (VI), $R^1$ is independently hydrogen or deuterium;

$R^2$ is independently hydrogen or deuterium;

$R^3$ is independently hydrogen or deuterium;

L is independently hydrogen, alkyl or (methoxycarbonyl)oxymethyl;

and, in each of the formula (I), formula (II), formula (III), formula (IV), formula (V), or formula (VI), at least one of $R^1$, $R^2$ and $R^3$ is deuterium.

4. The polycyclic carbamoylpyridone derivative as shown in formula (I), formula (II), formula (III), formula (IV), formula (V), or formula (VI), the stereoisomer thereof, the tautomer thereof, the hydrate thereof, the solvate thereof, the crystal form thereof, the pharmaceutically acceptable salt thereof, or the prodrug thereof as defined in claim 3, wherein, the polycyclic carbamoylpyridone derivative as shown in formula (I) is selected from the group consisting of:

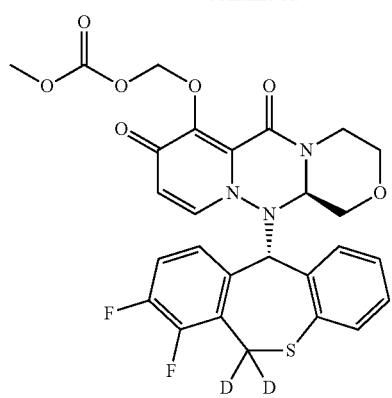
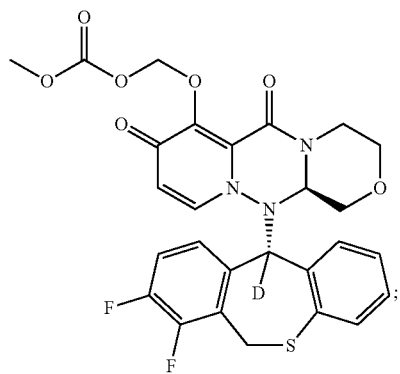
or, the polycyclic carbamoylpyridone derivative as shown in formula (II) is selected from the group consisting of:
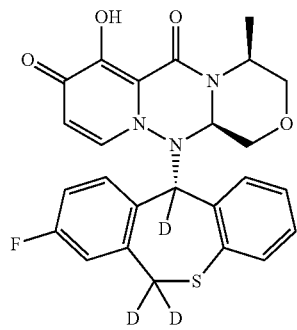
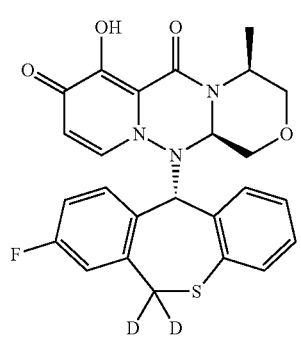 [SMILES: [2H]C1([2H])Sc2ccccc2[C@@H](N2[C@@H]3COC[C@H](C)N3C(=O)c3c(O)c(=O)ccn32)c2ccc(F)cc21]
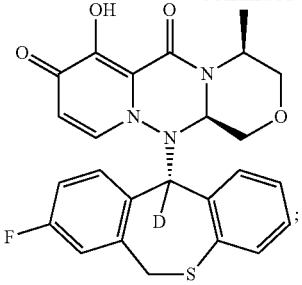
or, the polycyclic carbamoylpyridone derivative as shown in formula (III) is selected from the group consisting of:
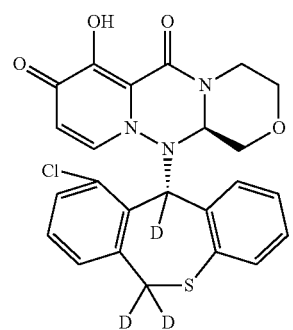
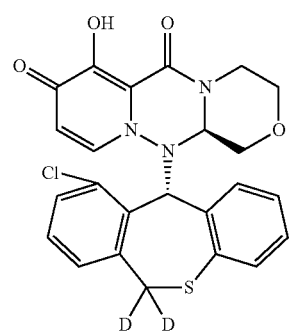 [SMILES: [2H]C1([2H])Sc2ccccc2[C@@H](N2[C@@H]3COCCN3C(=O)c3c(O)c(=O)ccn32)c2c(Cl)cccc21]
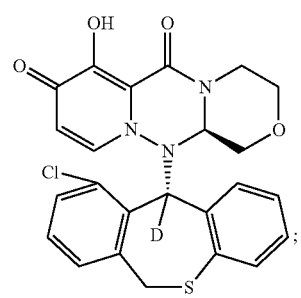
or, the polycyclic carbamoylpyridone derivative as shown in formula (IV) is selected from the group consisting of:

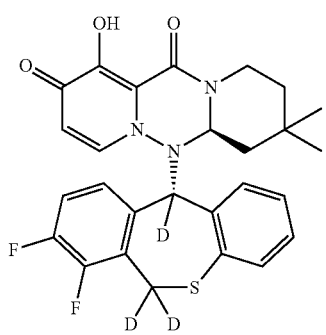
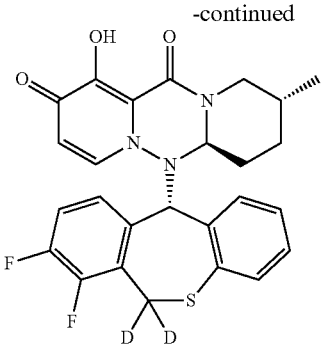
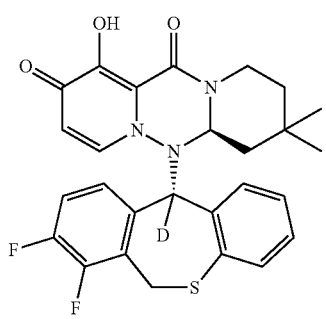
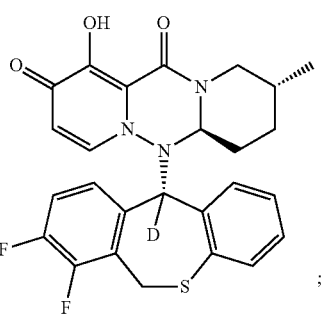
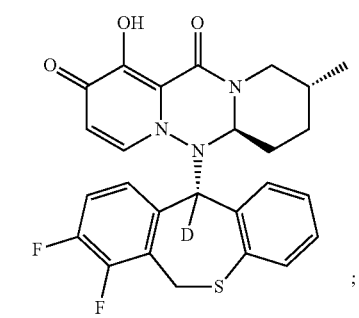
or, the polycyclic carbamoylpyridone derivative as shown in formula (VI) is selected from the group consisting of:
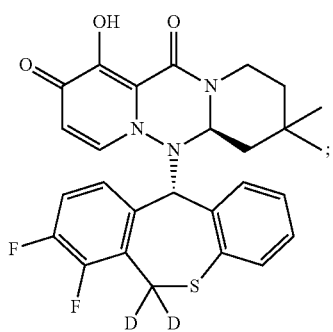
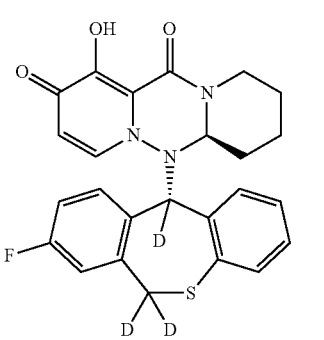
or, the polycyclic carbamoylpyridone derivative as shown in formula (V) is selected from the group consisting of:
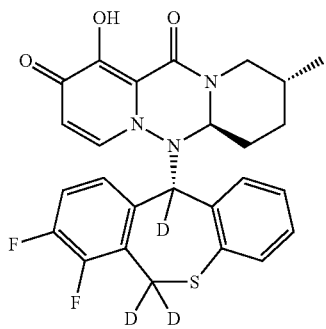
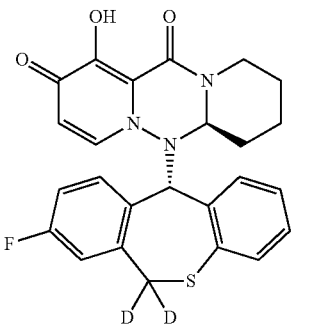 [SMILES: [2H]C1([2H])Sc2ccccc2[C@@H](N2[C@@H]3CCCCN3C(=O)c3c(O)c(=O)ccn32)c2ccc(F)cc21]

-continued

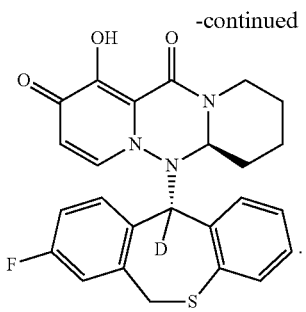

5. The polycyclic carbamoylpyridone derivative, the stereoisomer thereof, the tautomer thereof, the hydrate thereof, the solvate thereof, the crystal form thereof, the pharmaceutically acceptable salt thereof, or the prodrug thereof as claimed in claim 1, wherein,
the pharmaceutically acceptable salt thereof is an acid addition salt formed by the polycyclic carbamoylpyridone derivative as shown in formula (VII) and an organic acid or an inorganic acid; wherein, the organic acid is one or more selected from the group consisting of maleic acid, fumaric acid, benzoic acid, ascorbic acid, succinic acid, methanesulfonic acid, acetic acid, trifluoroacetic acid, oxalic acid, propionic acid, tartaric acid, salicylic acid, citric acid, gluconic acid, lactic acid, mandelic acid, phenylacetic acid, aspartic acid, stearic acid, palmitic acid, glycolic acid, glutamic acid and benzenesulfonic acid; the inorganic acid is one or more selected from the group consisting of hydrochloric acid, hydrobromic acid, sulfuric acid, phosphoric acid and nitric acid;
or, the pharmaceutically acceptable salt thereof is a salt formed by the polycyclic carbamoylpyridone derivative as shown in formula (VII) and one or more organic and inorganic cations selected from the group consisting of alkali metal ions, alkaline earth metal ions and ammonium ions; wherein, the alkali metal is selected from lithium, sodium, or potassium; and the alkaline earth metal is selected from magnesium, barium, or calcium.

6. A pharmaceutical composition comprising a therapeutically effective amount of the polycyclic carbamoylpyridone derivative, the stereoisomer thereof, the tautomer thereof, the hydrate thereof, the solvate thereof, the crystal form thereof, the pharmaceutically acceptable salt thereof, or the prodrug thereof as defined in claim 1, and a pharmaceutically acceptable carrier.

7. The pharmaceutical composition as defined in claim 6, further comprising other active pharmaceutical ingredient, and the other active pharmaceutical ingredient is selected from neuraminidase inhibitors, RNA-dependent RNA polymerase inhibitors, M2 protein inhibitors, PB2 Cap binding inhibitors, anti-HA antibodies, or immune action drugs.

8. The pharmaceutical composition as defined in claim 7, wherein the neuraminidase inhibitor is oseltamivir, zanamivir, peramivir, or Inavir; the RNA-dependent RNA polymerase inhibitor is favipiravir; the M2 protein inhibitor is amantadine; the PB2 Cap binding inhibitor is VX-787; the anti-HA antibody is MHAA4594A; the immune action drug is nitazoxanide.

9. A method for treating and/or alleviating a disease in an individual in need thereof, comprising: administering an effective amount of the polycyclic carbamoylpyridone derivative, the stereoisomer thereof, the tautomer thereof, the hydrate thereof, the solvate thereof, the crystal form thereof, the pharmaceutically acceptable salt thereof, or the prodrug thereof as defined in claim 1 to the individual to inhibit the in vivo level of 5'cap-dependent endonuclease of the individual, wherein the disease refers to a symptom and/or disease caused by influenza virus infection.

10. The method as defined in claim 9, wherein the influenza virus is selected from type A, type B, or type C.

11. The method as defined in claim 9, wherein the symptom is selected from cold-like symptoms of fever, chill, headache, muscle pain, general fatigue, and the like, or respiratory tract inflammations of sore throat, runny nose, nasal congestion, cough, sputum; gastrointestinal symptoms of abdominal pain, vomiting, diarrhea; and further complications of secondary infection of acute encephalopathy, pneumonia.

12. The polycyclic carbamoylpyridone derivative, the stereoisomer thereof, the tautomer thereof, the hydrate thereof, the solvate thereof, the crystal form thereof, the pharmaceutically acceptable salt thereof, or the prodrug thereof as defined in claim 3, wherein,
the pharmaceutically acceptable salt thereof is an acid addition salt formed by the polycyclic carbamoylpyridone derivative as shown in formula (I), formula (II), formula (III), formula (IV), formula (V), or formula (VI) and an organic acid or an inorganic acid; wherein, the organic acid is one or more selected from the group consisting of maleic acid, fumaric acid, benzoic acid, ascorbic acid, succinic acid, methanesulfonic acid, acetic acid, trifluoroacetic acid, oxalic acid, propionic acid, tartaric acid, salicylic acid, citric acid, gluconic acid, lactic acid, mandelic acid, phenylacetic acid, aspartic acid, stearic acid, palmitic acid, glycolic acid, glutamic acid and benzenesulfonic acid; the inorganic acid is one or more selected from the group consisting of hydrochloric acid, hydrobromic acid, sulfuric acid, phosphoric acid and nitric acid;
or, the pharmaceutically acceptable salt thereof is a salt formed by the polycyclic carbamoylpyridone derivative as shown in formula (I), formula (II), formula (III), formula (IV), formula (V), or formula (VI) and one or more organic and inorganic cations selected from the group consisting of alkali metal ions, alkaline earth metal ions and ammonium ions; wherein, the alkali metal is selected from lithium, sodium, or potassium; and the alkaline earth metal is selected from magnesium, barium, or calcium.

13. The polycyclic carbamoylpyridone derivative, the stereoisomer thereof, the tautomer thereof, the hydrate thereof, the solvate thereof, the crystal form thereof, the pharmaceutically acceptable salt thereof, or the prodrug thereof as defined in claim 4, wherein,
the pharmaceutically acceptable salt thereof is an acid addition salt formed by the polycyclic carbamoylpyridone derivative as shown in formula (I), formula (II), formula (III), formula (IV), formula (V), or formula (VI) and an organic acid or an inorganic acid; wherein, the organic acid is one or more selected from the group consisting of maleic acid, fumaric acid, benzoic acid, ascorbic acid, succinic acid, methanesulfonic acid, acetic acid, trifluoroacetic acid, oxalic acid, propionic acid, tartaric acid, salicylic acid, citric acid, gluconic acid, lactic acid, mandelic acid, phenylacetic acid, aspartic acid, stearic acid, palmitic acid, glycolic acid, glutamic acid and benzenesulfonic acid; the inorganic acid is one or more selected from the group consisting of hydrochloric acid, hydrobromic acid, sulfuric acid, phosphoric acid and nitric acid;

or, the pharmaceutically acceptable salt thereof is a salt formed by the polycyclic carbamoylpyridone derivative as shown in formula (I), formula (II), formula (III), formula (IV), formula (V), or formula (VI) and one or more organic and inorganic cations selected from the group consisting of alkali metal ions, alkaline earth metal ions and ammonium ions; wherein, the alkali metal is selected from lithium, sodium, or potassium; and the alkaline earth metal is selected from magnesium, barium, or calcium.

14. A pharmaceutical composition comprising a therapeutically effective amount of the polycyclic carbamoylpyridone derivative, the stereoisomer thereof, the tautomer thereof, the hydrate thereof, the solvate thereof, the crystal form thereof, the pharmaceutically acceptable salt thereof, or the prodrug thereof as defined in claim 3, and a pharmaceutically acceptable carrier.

15. The pharmaceutical composition as defined in claim 14, further comprising other active pharmaceutical ingredient, and the other active pharmaceutical ingredient is selected from neuraminidase inhibitors, RNA-dependent RNA polymerase inhibitors, M2 protein inhibitors, PB2 Cap binding inhibitors, anti-HA antibodies, or immune action drugs.

16. A pharmaceutical composition comprising a therapeutically effective amount of the polycyclic carbamoylpyridone derivative, the stereoisomer thereof, the tautomer thereof, the hydrate thereof, the solvate thereof, the crystal form thereof, the pharmaceutically acceptable salt thereof, or the prodrug thereof as defined in claim 4, and a pharmaceutically acceptable carrier.

17. The pharmaceutical composition as defined in claim 16, further comprising other active pharmaceutical ingredient, and the other active pharmaceutical ingredient is selected from neuraminidase inhibitors, RNA-dependent RNA polymerase inhibitors, M2 protein inhibitors, PB2 Cap binding inhibitors, anti-HA antibodies, or immune action drugs.

18. A method for treating, and/or alleviating a disease in an individual in need thereof, comprising: administering an effective amount of the polycyclic carbamoylpyridone derivative, the tautomer thereof, the hydrate thereof, the solvate thereof, the active metabolite thereof, the crystal form thereof, the pharmaceutically acceptable salt thereof, or the prodrug thereof as defined in claim 3 to the individual to inhibit the in vivo level of 5'cap-dependent endonuclease of the individual, wherein the disease refers to a symptom and/or disease caused by influenza virus infection.

19. A method for treating and/or alleviating a disease in an individual in need thereof, comprising: administering an effective amount of the polycyclic carbamoylpyridone derivative, the stereoisomer thereof, the tautomer thereof, the hydrate thereof, the solvate thereof, the crystal form thereof, the pharmaceutically acceptable salt thereof, or the prodrug thereof as defined in claim 4 to the individual to inhibit the in vivo level of 5'cap-dependent endonuclease of the individual, wherein the disease refers to a symptom and/or disease caused by influenza virus infection.

\* \* \* \* \*